(12) United States Patent
Benayahu et al.

(10) Patent No.: US 8,747,484 B2
(45) Date of Patent: Jun. 10, 2014

(54) METHOD OF REGENERATING CONNECTIVE TISSUE WITH A SCAFFOLD OF CORAL-DERIVED COLLAGEN

(71) Applicants: Ramot at Tel-Aviv University Ltd., Tel-Aviv (IL); Technion Research & Development Foundation Limited, Haifa (IL)

(72) Inventors: Yehuda Benayahu, Herzlia (IL); Dafna Benayahu, Herzlia (IL); Yoel Kashman, Tel-Aviv (IL); Amira Rudi, Ramat-HaSharon (IL); Yoram Lanir, Haifa (IL); Ido Sella, Mevaseret Zion (IL); Einat Raz, Mitzpe Aviv (IL)

(73) Assignees: Ramot at Tel-Aviv University Ltd., Tel-Aviv (IL); Technion Research & Development Foundation Limited, Haifa (IL)

( * ) Notice: Subject to any disclaimer, the term of this patent is extended or adjusted under 35 U.S.C. 154(b) by 0 days.

(21) Appl. No.: 13/944,917

(22) Filed: Jul. 18, 2013

(65) Prior Publication Data
US 2013/0302895 A1 Nov. 14, 2013

Related U.S. Application Data

(62) Division of application No. 12/934,704, filed as application No. PCT/IL2009/000334 on Mar. 25, 2009, now Pat. No. 8,552,153.

(60) Provisional application No. 61/064,792, filed on Mar. 27, 2008.

(51) Int. Cl.
*A61F 2/02* (2006.01)

(52) U.S. Cl.
USPC .................. 623/23.72; 530/356; 435/398

(58) Field of Classification Search
None
See application file for complete search history.

(56) References Cited

U.S. PATENT DOCUMENTS

| 2006/0210601 A1 | 9/2006 | Yunoki et al. |
| 2011/0038914 A1 | 2/2011 | Benayahu et al. |

FOREIGN PATENT DOCUMENTS

| FR | 2714063 | 6/1995 |
| WO | WO 2009/118734 | 10/2009 |

OTHER PUBLICATIONS

Communication Pursuant to Article 94(3) EPC Dated Jun. 12, 2012 From the European Patent Office Re. Application No. 09725189.6.
Communication Pursuant to Article 94(3) EPC Dated Feb. 25, 2011 From the European Patent Office Re. Application No. 09725189.6.
Communication Relating to the Results of the Partial International Search Dated Aug. 4, 2009 From the International Searching Authority Re.: Application No. PCT/IL2009/000334.
International Preliminary Report on Patentability Dated Oct. 7, 2010 From the International Bureau of WIPO Re. Application No. PCT/IL2009/000334.
International Search Report and the Written Opinion Dated Oct. 5, 2009 From the International Searching Authority Re.: Application No. PCT/IL2009/000334.
Notice of Allowance Dated Apr. 8, 2013 From the US Patent and Trademark Office Re. U.S. Appl. No. 12/934,704.
Office Action Dated Sep. 10, 2012 From the Israel Patent Office Re. Application No. 208275 and Its Translation Into English.
Official Action Dated Jan. 19, 2012 From the US Patent and Trademark Office Re. U.S. Appl. No. 12/934,704.
Adams "Invertebrate Collagens. Marked Differences From Vertebrate Collagens Appear in Only a Few Vertebrate Groups", Science, XP002538529, 202(4368): 591-598, Nov. 10, 1978. Table 1.
Tillet-Barret et al. "Characterization of Heterotrimeric Collagen Molecules in a Sea-Pen (Cnideria, Octocorallia)", European Journal of Biochemistry / FEBS, XP002538528, 203(1-2): 179-184, Jan. 15, 1992.
Walker et al. "Sponges, Cnidarians and Worms: Simple Reef Invertebrates. Cnidarians: Soft Corals", The Coral Reef (Life in the Sea), Chap.3: 50-51, 2005.
Young "Collagen and Other Mesoglea Protein From the Coral *Lobophyllia corymbosa* (Anthozoa, Scleractinia)", International Journal of Biochemistry, XP023411356, 4(22): 339-344, Jan. 1, 1973.

*Primary Examiner* — Jon P Weber
*Assistant Examiner* — Robert Yamasaki

(57) ABSTRACT

A method is disclosed for regenerating connective tissue by administering a scaffold comprising collagen fibers extracted from a soft coral. The length of the soft coral collagen fibers following stretching by about 15% is identical to the length of the fibers prior to stretching.

10 Claims, 45 Drawing Sheets
(31 of 45 Drawing Sheet(s) Filed in Color)

Peak Results

|    | Name | RT     | Area    | Height | Amount  | Units    |
|----|------|--------|---------|--------|---------|----------|
| 1  |      | 11.787 | 1424008 | 94425  |         |          |
| 2  | AMQ  | 12.574 | 256468  | 12471  | 52.791  | picomole |
| 3  | Asp  | 13.625 | 2006364 | 117129 | 153.192 | picomole |
| 4  | Ser  | 15.340 | 1385631 | 91763  | 82.915  | picomole |
| 5  | Glu  | 16.009 | 2599459 | 153105 | 178.886 | picomole |
| 6  | Gly  | 17.486 | 7484000 | 399380 | 481.563 | picomole |
| 7  | His  | 18.261 | 539974  | 32272  | 21.965  | picomole |
| 8  | NH3  | 20.046 | 4163140 | 214314 | 147.737 | picomole |
| 9  |      | 21.299 | 154587  | 14556  |         |          |
| 10 | Arg  | 21.666 | 2240053 | 196436 | 99.123  | picomole |
| 11 | Thr  | 21.965 | 1460615 | 112141 | 64.337  | picomole |
| 12 |      | 22.810 | 51827   | 6490   |         |          |
| 13 | Ala  | 23.110 | 2709328 | 208734 | 117.246 | picomole |
| 14 |      | 24.348 | 45030   | 3694   |         |          |
| 15 | Pro  | 25.037 | 1047130 | 94664  | 97.042  | picomole |
| 16 |      | 26.543 | 23730   | 2665   |         |          |
| 17 |      | 27.843 | 21139   | 2759   |         |          |
| 18 |      |        |         |        |         |          |
| 19 | Tyr  | 28.349 | 634440  | 76888  | 26.206  | picomole |
| 20 |      | 28.914 | 110796  | 11476  |         |          |
| 21 | Val  | 29.295 | 3173320 | 312675 | 71.826  | picomole |
| 22 | Met  | 29.789 | 697573  | 82471  | 20.148  | picomole |
| 23 |      | 30.375 | 35251   | 3603   |         |          |
| 24 |      | 31.109 | 56932   | 5361   |         |          |
| 25 | Lys  | 31.853 | 1140838 | 129685 | 48.668  | picomole |
| 26 | Ile  | 32.447 | 2381041 | 247277 | 42.460  | picomole |
| 27 | Leu  | 32.869 | 3287720 | 343442 | 58.855  | picomole |
| 28 | Phe  | 33.704 | 1753712 | 189860 | 24.630  | picomole |
| 29 |      | 34.571 | 38430   | 4817   |         |          |

FIG. 2A

| Amino Acid | aaa346 | nmoles aa | μgrams | mole percent | # residues (if 50k protein) |
|---|---|---|---|---|---|
| cysac | | | | | |
| cmcys | | | | | |
| asx | 97.2071 | 97.207 | 11.188 | 9.1% | 50.1 |
| thr | 32.1071 | 32.107 | 3.246 | 3.0% | 16.6 |
| ser | 47.1984 | 47.198 | 4.110 | 4.4% | 24.3 |
| glx | 112.2617 | 112.262 | 14.383 | 10.5% | 57.9 |
| pro+cys | 68.0893 | 68.089 | 6.613 | 6.4% | 35.1 |
| gly | 420.3537 | 420.354 | 23.981 | 39.3% | 216.7 |
| ala | 76.6377 | 76.638 | 5.447 | 7.2% | 39.5 |
| val | 41.0179 | 41.018 | 4.066 | 3.8% | 21.1 |
| met | 10.8536 | 10.854 | 1.424 | 1.0% | 5.6 |
| ileu | 23.1293 | 23.129 | 2.617 | 2.2% | 11.9 |
| leu | 33.8585 | 33.859 | 3.831 | 3.2% | 17.5 |
| tyr | 13.0019 | 13.002 | 2.122 | 1.2% | 6.7 |
| phe | 13.4557 | 13.456 | 1.980 | 1.3% | 6.9 |
| his | deleted | | | | |
| lys | 24.2554 | 24.255 | 3.109 | 2.3% | 12.5 |
| trp | | | | | |
| arg | 56.8384 | 56.838 | 8.878 | 5.3% | 29.3 |
| % injected | 100% | | | total residues: | 552 |

FIG. 11

| Amino Acid | aaa347 | nmoles aa | µgrams | mole percent | # residues (if 50K protein) |
|---|---|---|---|---|---|
| cysac | | | | | |
| cmcys | | | | | |
| asx | 84.4336 | 84.434 | 9.717 | 9.4% | 51.8 |
| thr | 28.1409 | 28.141 | 2.845 | 3.1% | 17.3 |
| ser | 40.6567 | 40.657 | 3.540 | 4.5% | 25.0 |
| glx | 96.2588 | 96.259 | 12.333 | 10.7% | 59.1 |
| pro+cys | 58.7064 | 58.706 | 5.702 | 6.5% | 36.0 |
| gly | 347.0740 | 347.074 | 19.801 | 38.6% | 213.1 |
| ala | 64.5424 | 64.542 | 4.588 | 7.2% | 39.6 |
| val | 35.7227 | 35.723 | 3.541 | 4.0% | 21.9 |
| met | 9.1274 | 9.127 | 1.198 | 1.0% | 5.6 |
| ileu | 20.1921 | 20.192 | 2.285 | 2.2% | 12.4 |
| leu | 29.8487 | 29.849 | 3.378 | 3.3% | 18.3 |
| tyr | 11.1990 | 11.199 | 1.827 | 1.2% | 6.9 |
| phe | 11.8123 | 11.812 | 1.739 | 1.3% | 7.3 |
| his | deleted | | | | |
| lys | 18.8266 | 18.827 | 2.413 | 2.1% | 11.6 |
| trp | | | | | |
| arg | 41.8918 | 41.892 | 6.543 | 4.7% | 25.7 |
| % injected | 100% | | | total residues: | 552 |

FIG. 12

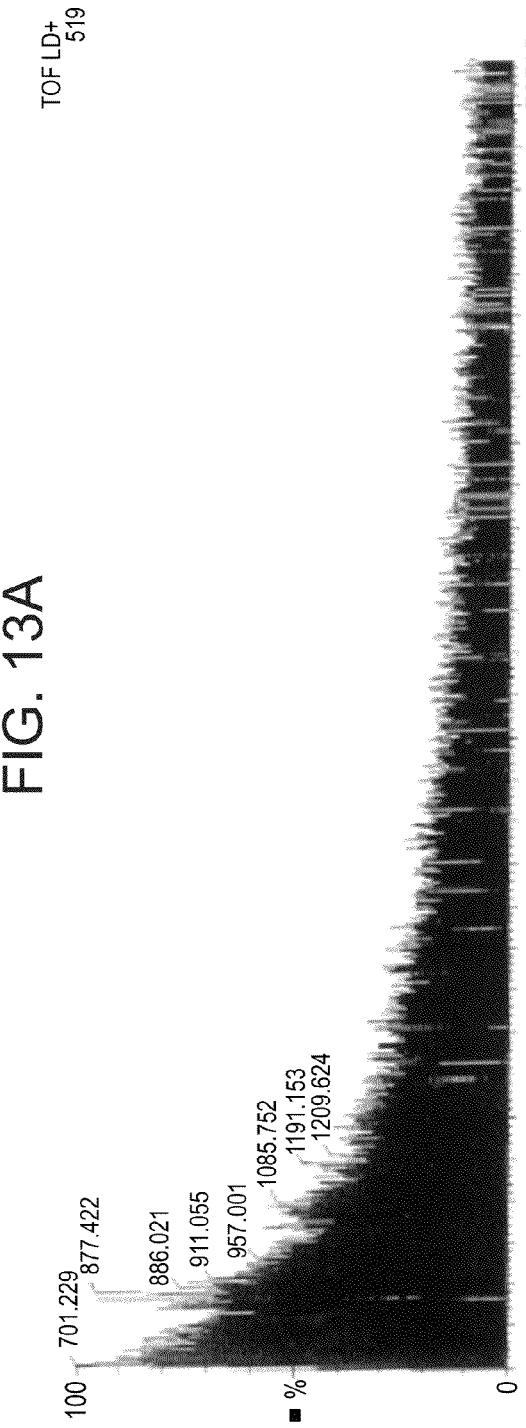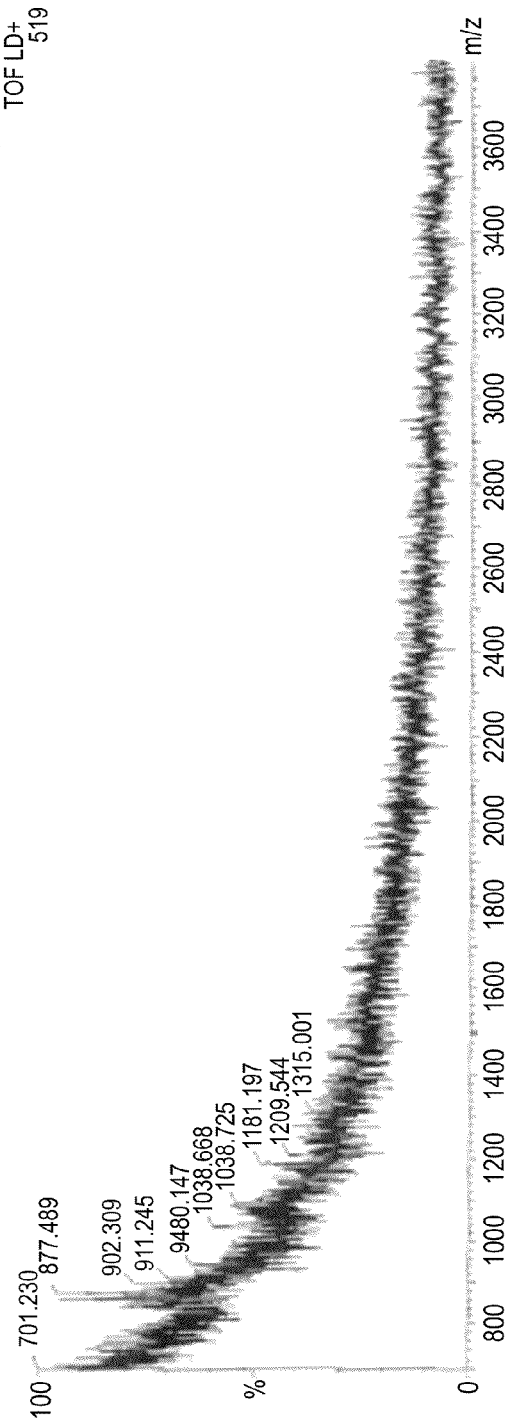

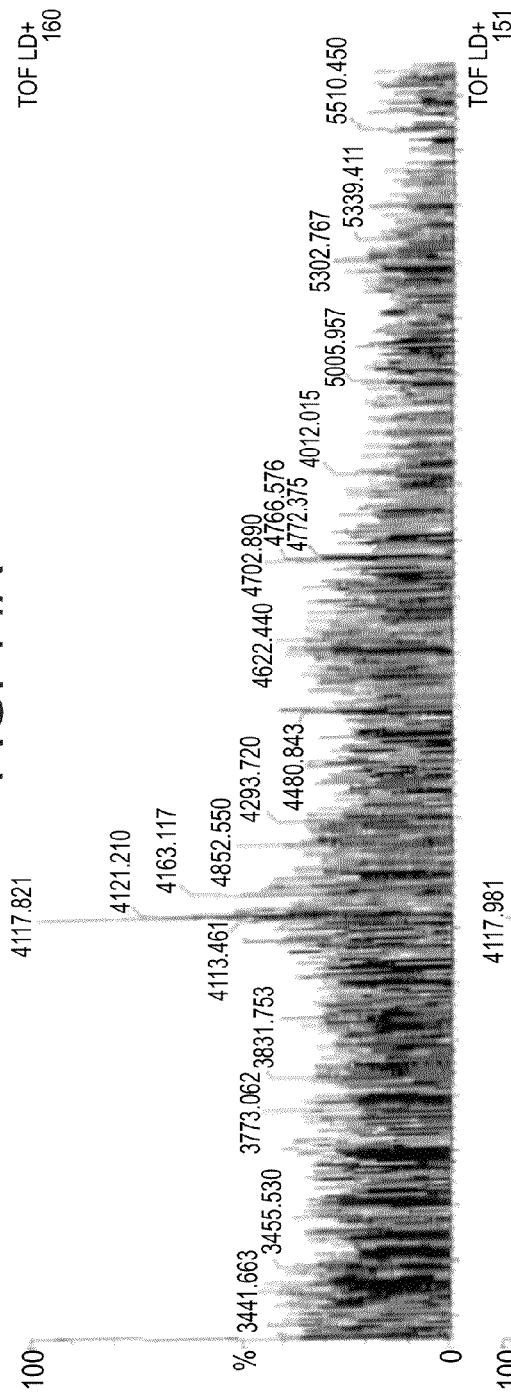
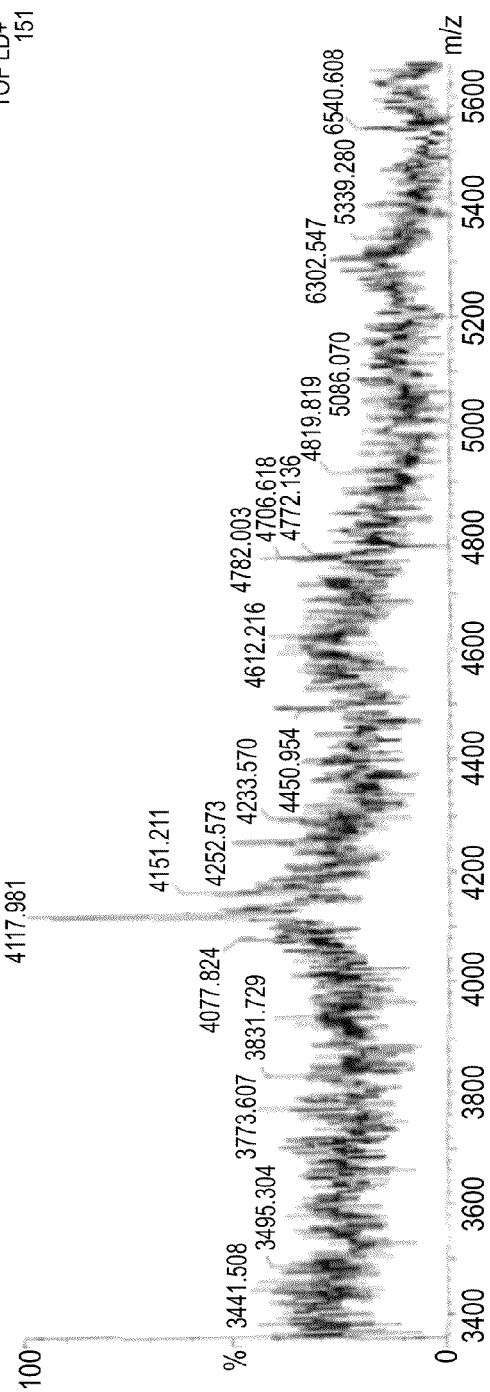
FIG. 14A
FIG. 14B

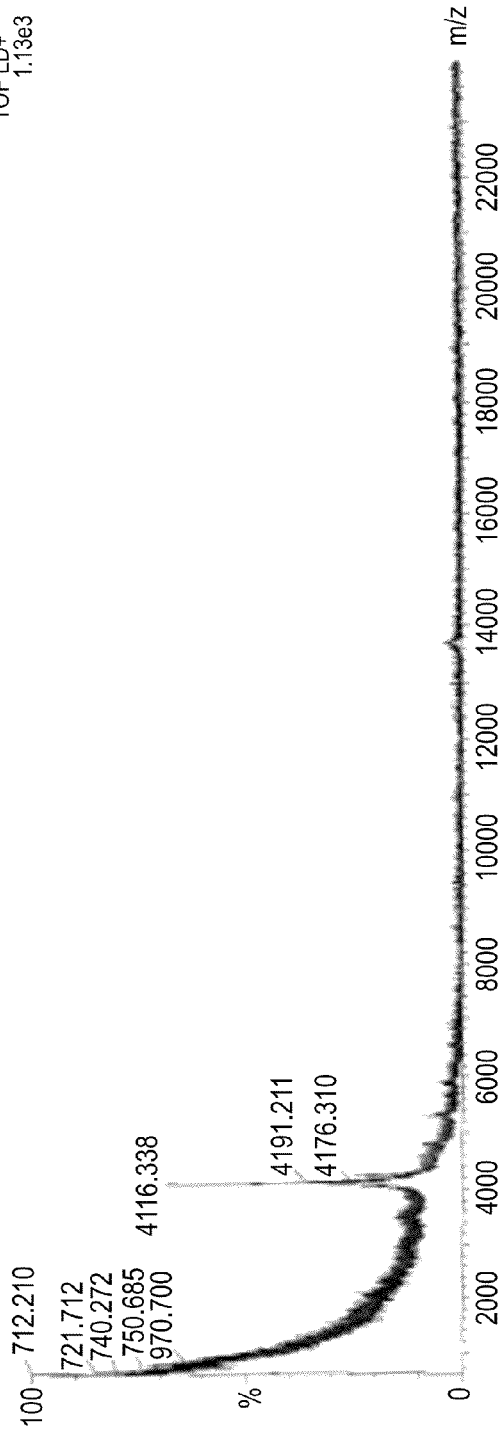

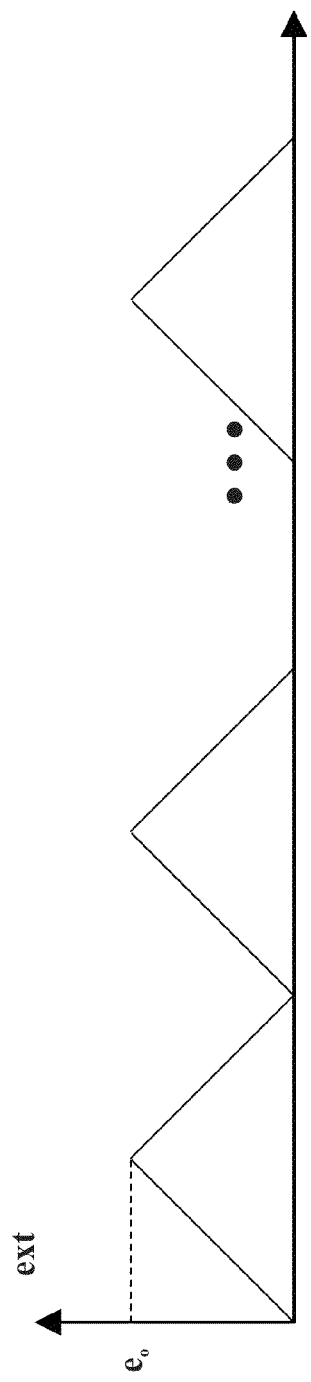

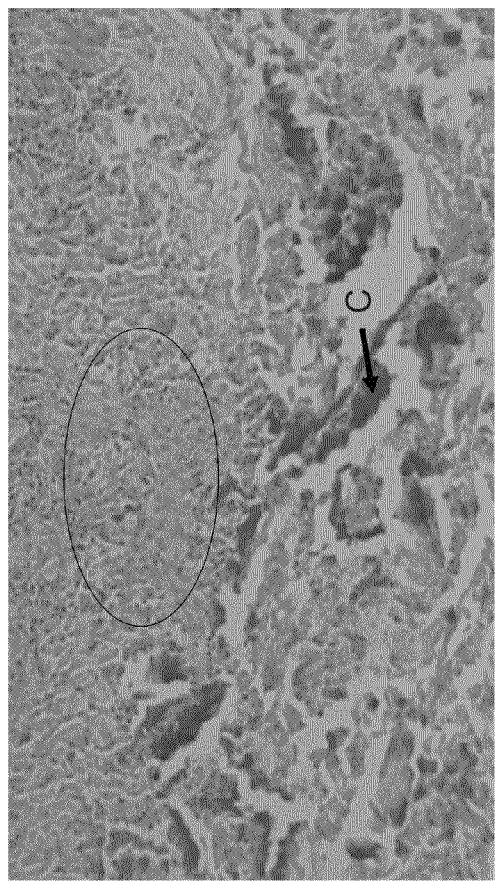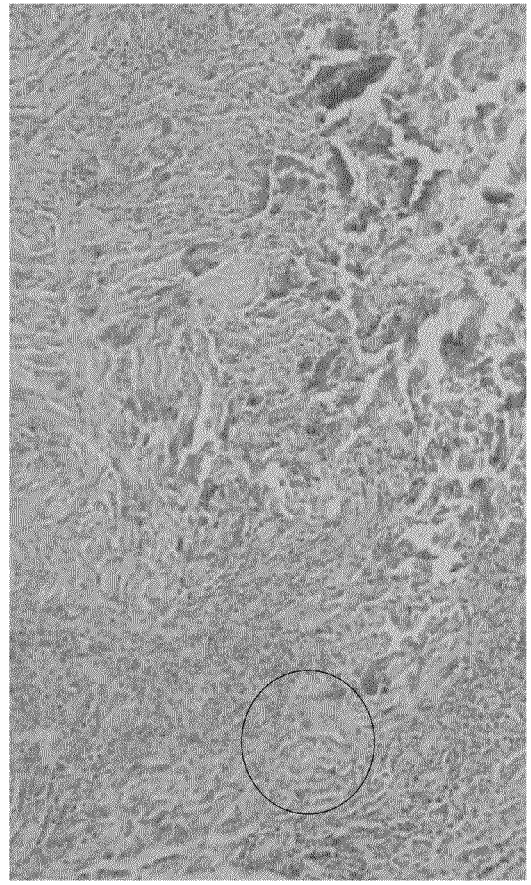
FIG. 31A
FIG. 31B

METHOD OF REGENERATING CONNECTIVE TISSUE WITH A SCAFFOLD OF CORAL-DERIVED COLLAGEN

RELATED APPLICATIONS

This Application is a division of U.S. patent application Ser. No. 12/934,704 filed on Oct. 28, 2010, which is a National Phase of PCT Patent Application No. PCT/IL2009/000334 having International filing date of Mar. 25, 2009, which claims the benefit of priority of U.S. Provisional Patent Application No. 61/064,792 filed on Mar. 27, 2008. The contents of the above Applications are all incorporated by reference as if fully set forth herein in their entirety.

FIELD AND BACKGROUND OF THE INVENTION

The present invention, in some embodiments thereof, relates to a collagen comprising enhanced elasticity and, more particularly, but not exclusively, to a coral-derived collagen.

Collagens are the main structural proteins responsible for the structural integrity of vertebrates and many other multicellular organisms.

Collagen provides biomaterials for a myriad of uses including pharmaceutical (haemostatic compresses, sponges, dressings in particular healing dressings), medical (prostheses such as cardiac valves, tendons and ligaments, skin substitutes, filling agents), odontological (gum implants) and cosmetic (additive, anti-wrinkling agent, microcontainer for perfumed substances). Collagen-based products can be made into membranes, films, sheets, sponges and dispersions of fibrils for any of the above purposes.

One important area in which collagen has proven useful is that of tissue engineering. Tissue engineering (TE) is defined as the application of engineering disciplines to either maintain existing tissue structures or to enable new tissue growth. This engineering approach generally includes the delivery of a tissue scaffold that serves as an architectural support onto which cells may attach, proliferate, and synthesize new tissue to repair a wound or defect. Tissue scaffolds typically have high open-celled porosity to allow cell migration throughout the scaffold and also to allow important nutrient-bearing fluids to flow through the scaffold to maintain the health of the cells.

Tissue engineering scaffolds that have been reported in the literature include meshes, woven structures, non-woven structures, knitted structures, three dimensional woven structures, sponges and foams. The scaffolds are typically made of materials that are biocompatible. Often, they are made of biodegradable materials. Biodegradable materials readily break down into small segments when exposed to moist body tissue. The segments then either are absorbed by the body, or passed by the body. More particularly, the biodegraded segments do not elicit permanent chronic foreign body reaction, because they are absorbed by the body or passed from the body, such that no permanent trace or residual of the segment is retained by the body. Ideally, the biodegradable tissue scaffolds degrade at approximately the same rate as the body synthesizes new tissue to repair the wound or defect.

A broad range of tissue engineering products based on collagen scaffolds are currently under development, and some of them have already reached the market. For example, collagen gels seeded with fibroblasts have been used as the "dermal" layer of the artificial skin sold under the tradename APLIGRAFT (Sandoz A G, Basel, Switzerland), and collagen sponges have been used as an osteoconductive carrier of bone morphogenic protein-2 (BMP-2) for spine fusion and the treatment of long bone fractures.

Collagen based biomaterials have been formed into fibers, film, sheets, sponges and dispersions of fibrils. Many of these forms could be used as tissue engineering scaffolds in the repair or augmentation of body tissue.

RELATED ART

U.S. Pat. No. 20050271614 teaches use of collagen of aquatic origin for cosmetic, pharmacological, dental, and cell culture products.

U.S. Pat. No. 20060210601 teaches a processed (non-native) collagen of enhanced elasticity and mechanical endurability.

Summary of the Invention

According to an aspect of some embodiments of the present invention there is provided an isolated collagen fiber, wherein a length of the fiber prior to stretching by about 15%, is identical to a length of the fiber following the stretching by about 15%.

According to an aspect of some embodiments of the present invention there is provided an isolated collagen fiber, comprising a Nuclear Magnetic Resonance (NMR) spectroscopic profile as shown in FIG. 1.

According to an aspect of some embodiments of the present invention there is provided an isolated collagen fiber being extracted from a soft coral *Sarcophyton* sp.

According to an aspect of some embodiments of the present invention there is provided a scaffold comprising the collagen of the present invention.

According to an aspect of some embodiments of the present invention there is provided a cell culture comprising mammalian cells seeded on the collagen of the present invention.

According to an aspect of some embodiments of the present invention there is provided a composite comprising, as a first component, the collagen fiber of the present invention and a second component selected from the group consisting of a mineral, a polysaccharide and a polypeptide.

According to an aspect of some embodiments of the present invention there is provided a method of regenerating tissue, the method comprising providing to a subject in need-thereof the scaffold of the present invention, thereby regenerating tissue.

According to an aspect of some embodiments of the present invention there is provided a method of farming a soft coral, the method comprising: (a) attaching the soft coral to a clay surface and (b) growing the soft coral on the clay surface under conditions which support propagation, thereby farming the soft coral.

According to an aspect of some embodiments of the present invention there is provided a pharmaceutical composition comprising the isolated collagen fiber of the present invention.

According to an aspect of some embodiments of the present invention there is provided a cosmetic composition comprising the isolated collagen fiber of the present invention.

According to an aspect of some embodiments of the present invention there is provided an isolated polypeptide comprising a Nuclear Magnetic Resonance (NMR) spectroscopic profile as shown in FIG. 1.

According to some embodiments of the invention, the isolated collagen fiber has an amino acid composition as shown in FIG. 2B.

According to some embodiments of the invention, the isolated collagen fiber is extracted from a coral.

According to some embodiments of the invention, the coral is *Sarcophyton* sp.

According to some embodiments of the invention, a fragment of the collagen comprises a major mass at about 4118.47 mass unit (MU).

According to some embodiments of the invention, the isolated collagen fiber comprises a Mass spectroscopy (MS) profile as shown in any one of FIGS. 13A-B-16A-B.

According to some embodiments of the invention, the isolated collagen fiber comprises a stiffness about 30-50% lower than that of mammalian collagen.

According to some embodiments of the invention, the isolated collagen fiber comprises a stiffness between about 0.34 GPa and 0.54 GPa.

According to some embodiments of the invention, the isolated collagen fiber comprises a tensile strength about half of mammalian collagen.

According to some embodiments of the invention, the isolated collagen fiber comprises a tensile strength between about 39-59 MPa.

According to some embodiments of the invention, each polypeptide of a triple helix of the collagen is separated by a 100 nm spacing.

According to some embodiments of the invention, the isolated collagen fiber is resistant to degradation by trypsin and collagenase.

According to some embodiments of the invention, the scaffold comprises (i) a support; and (ii) a layer being attached to at least part of a surface of the support, the layer comprising the collagen of the present invention.

According to some embodiments of the invention, the scaffold further comprising cells.

According to some embodiments of the invention, the conditions comprise a water temperature at a range of about 20-26° C. under a light intensity range of about 35-130 μE.

According to some embodiments of the invention, the conditions comprise a pH of about 8.2.

According to some embodiments of the invention, when the temperature is about 20° C., the light intensity is about 230 μE.

According to some embodiments of the invention, when the temperature is about 26° C., the light intensity is about 250 μE.

According to some embodiments of the invention, the method further comprises cutting the soft coral into pieces of less than 50 mm² and greater than 25 mm² prior to the attaching.

According to some embodiments of the invention, the attaching is effected using a glue.

According to some embodiments of the invention, the soft coral is of the *Sarcophyton* genus.

According to some embodiments of the invention, the soft coral comprises *Sarcophyton* sp or *Sarcophyton glaucum*.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 is a table illustrating the results of proton and carbon NMR analysis of the collagen of the present invention.

Figure 2B:
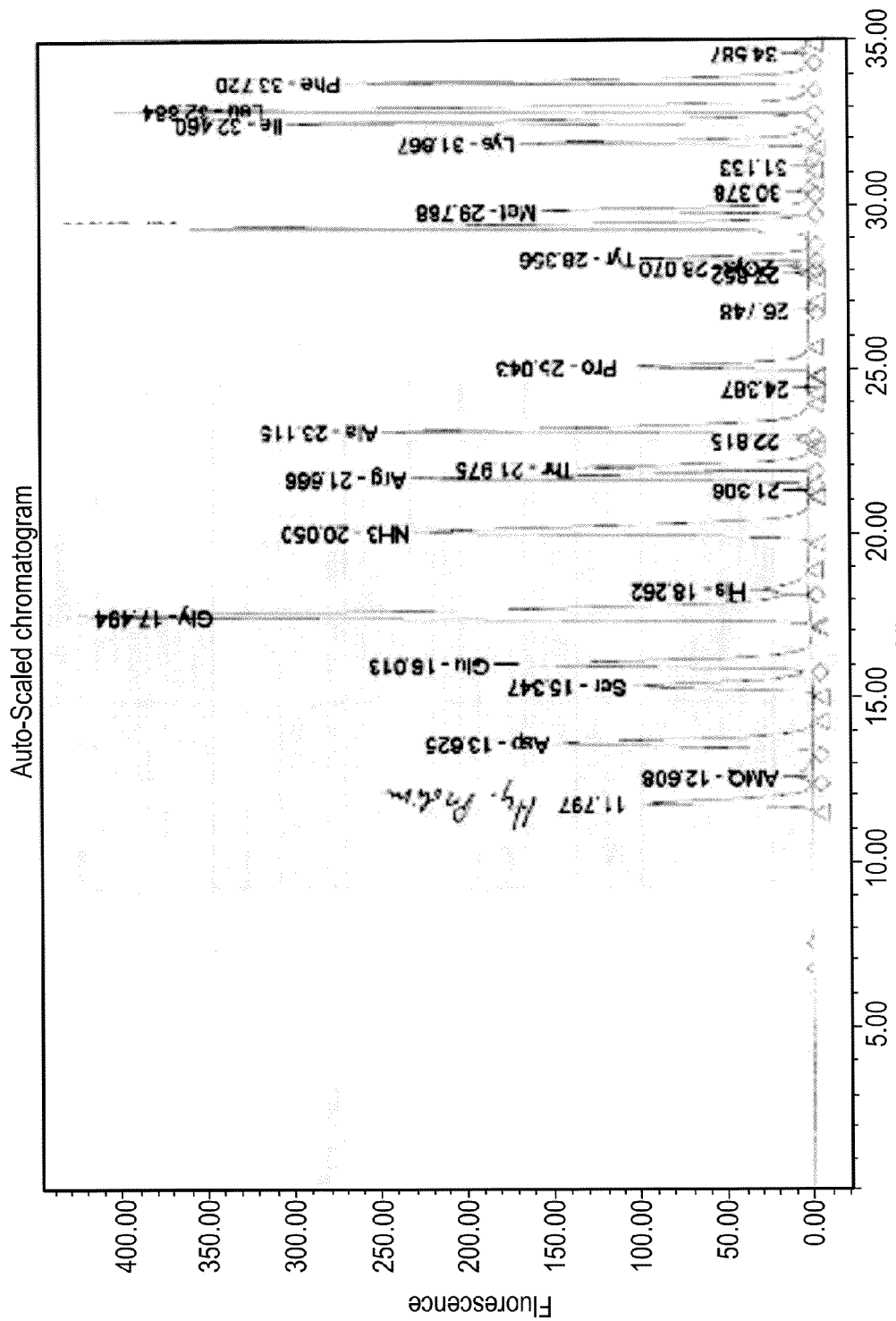

FIGS. 2A-B illustrate the results of amino acid analysis of the collagen of the present invention.

Figure 3:
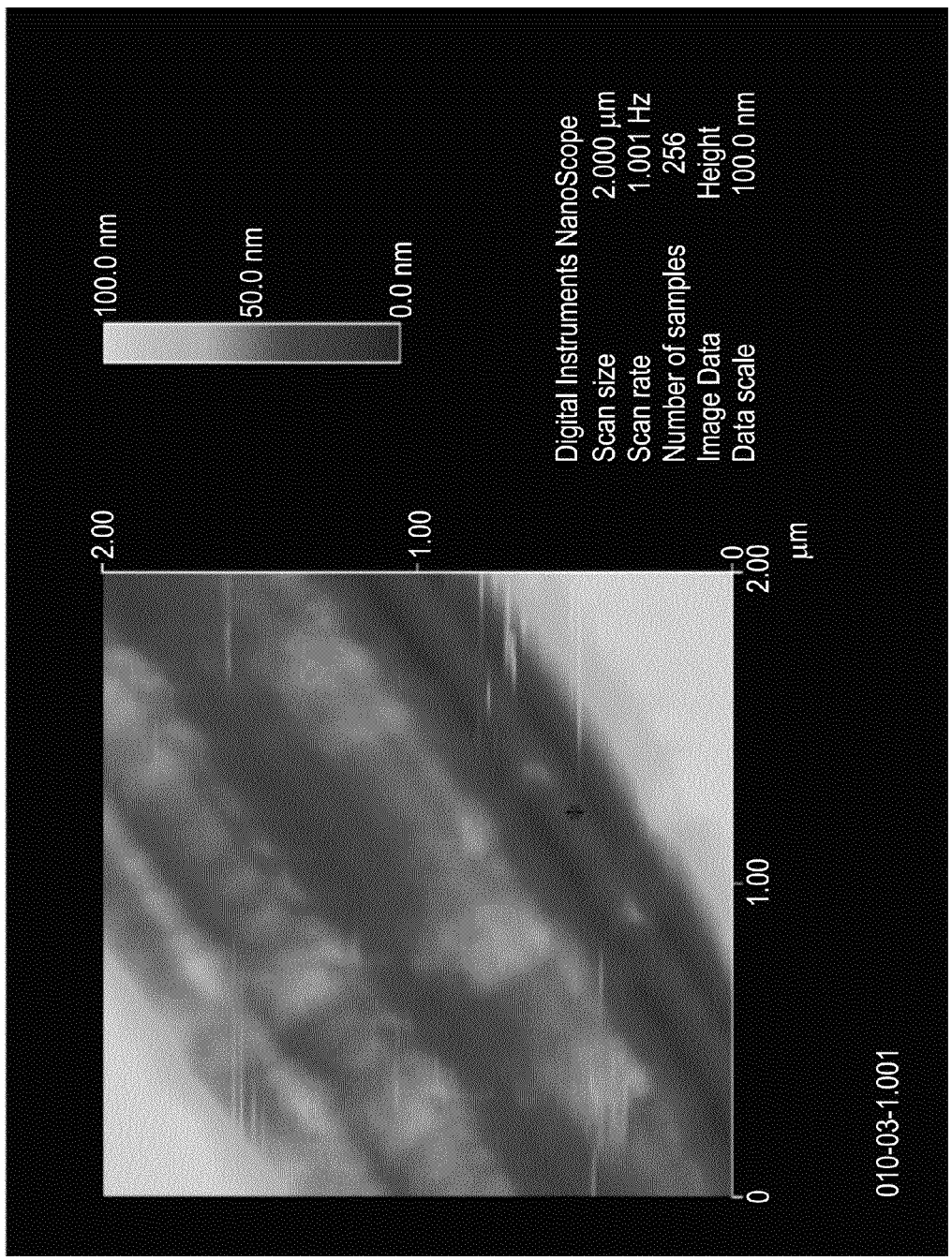

FIG. 3 is an image of isolated collagen. Fibrils are clearly present running from the lower left of the frame to the upper right of the frame. A "*" marks a fibril with ~100 nm spacing.

Figure 4A:
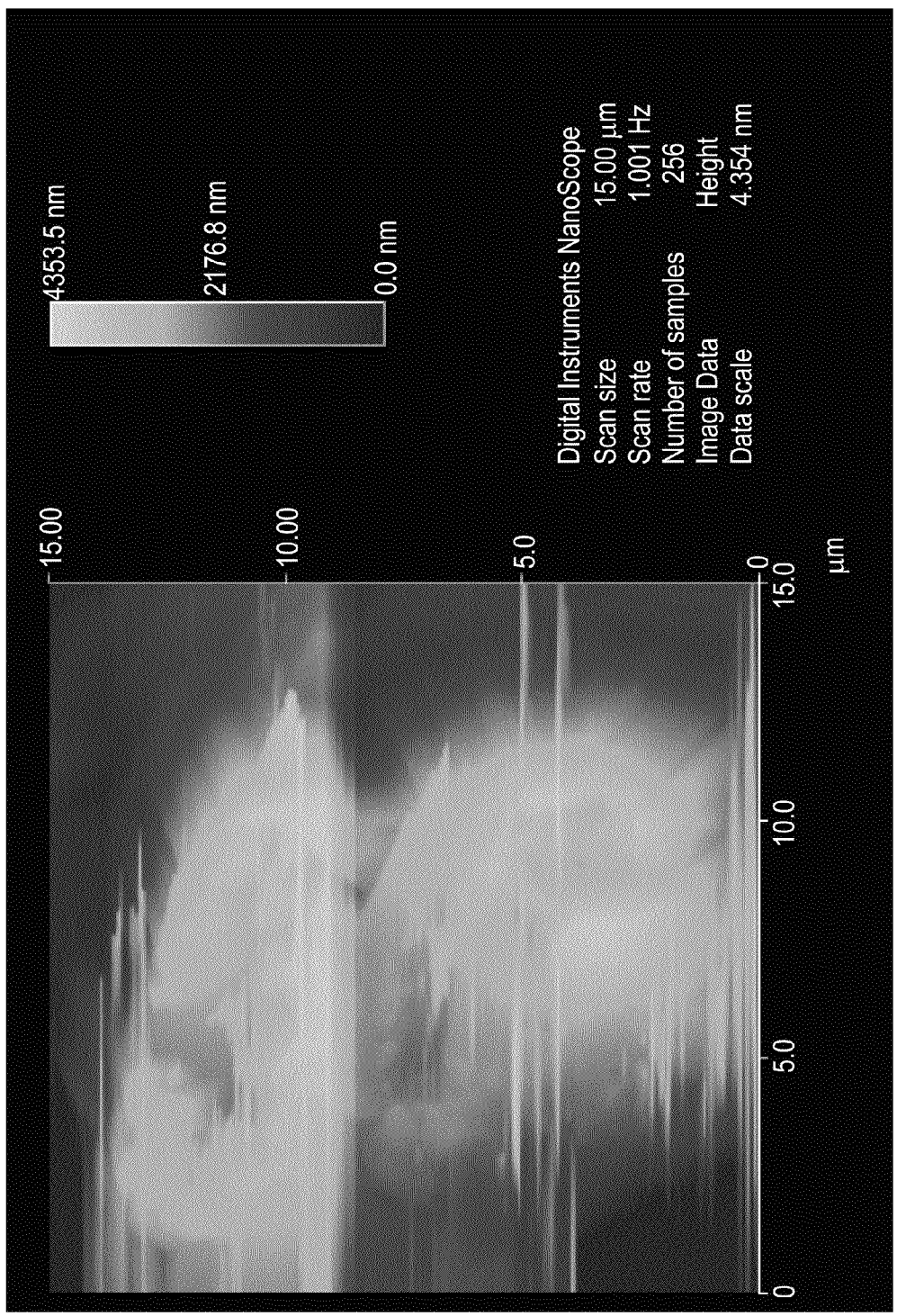
Figure 4B:
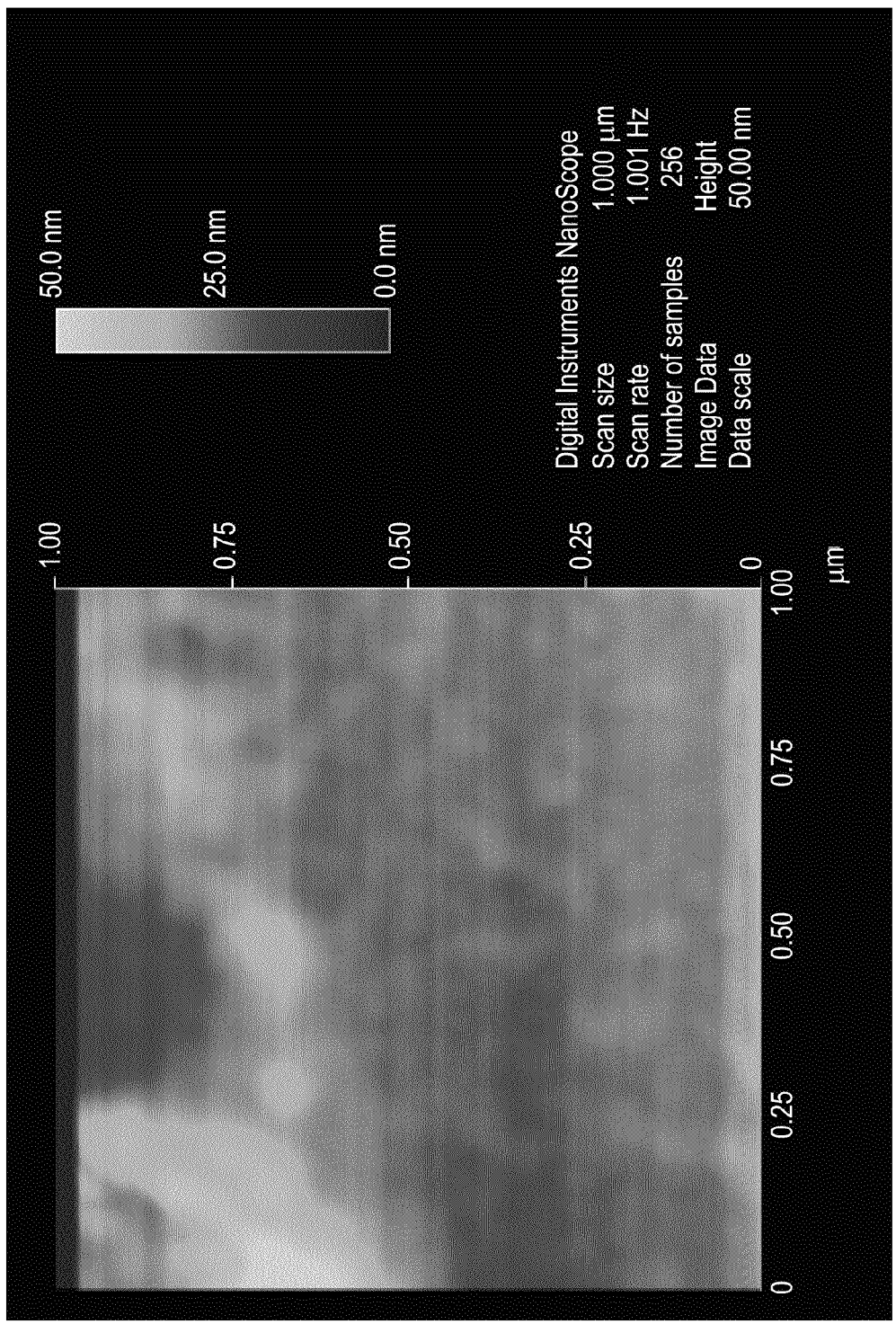

FIGS. 4A-B are image from small fixed samples of the collagen of the present invention. No fibrillar organization is present at the 15 μm scale isolated collagen (FIG. 4A) or at the 1 μm scale (FIG. 4B).

Figure 5:
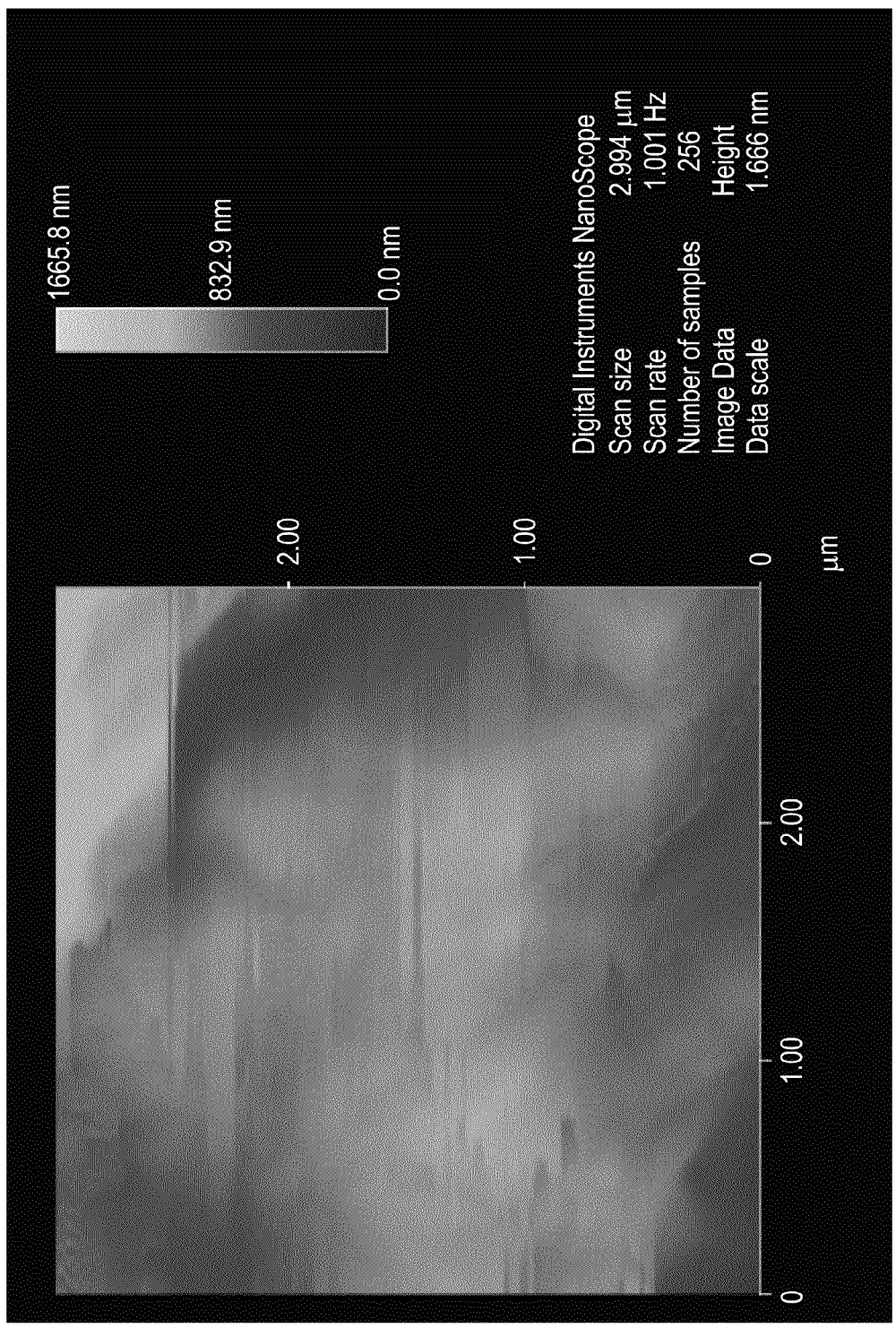

FIG. 5 is an image from a large unfixed sample of the collagen of the present invention. Probe placement was difficult and no fibrillar organization was present at the 3 μm scale.

Figure 6:
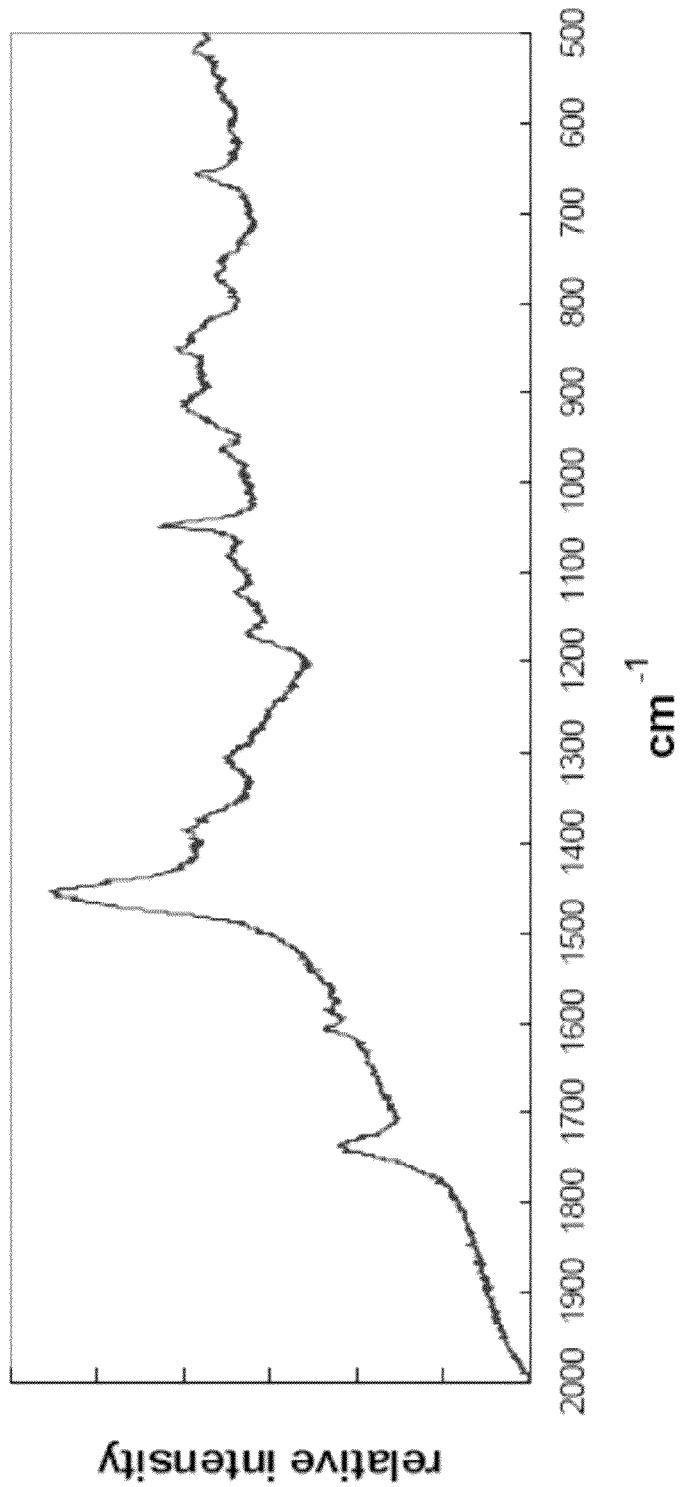

FIG. 6 is a Raman spectrum obtained from an isolated collagen sample.

Figure 7:

FIG. 7 is an example of image data from a collagen sample of the present invention.

Figure 8:
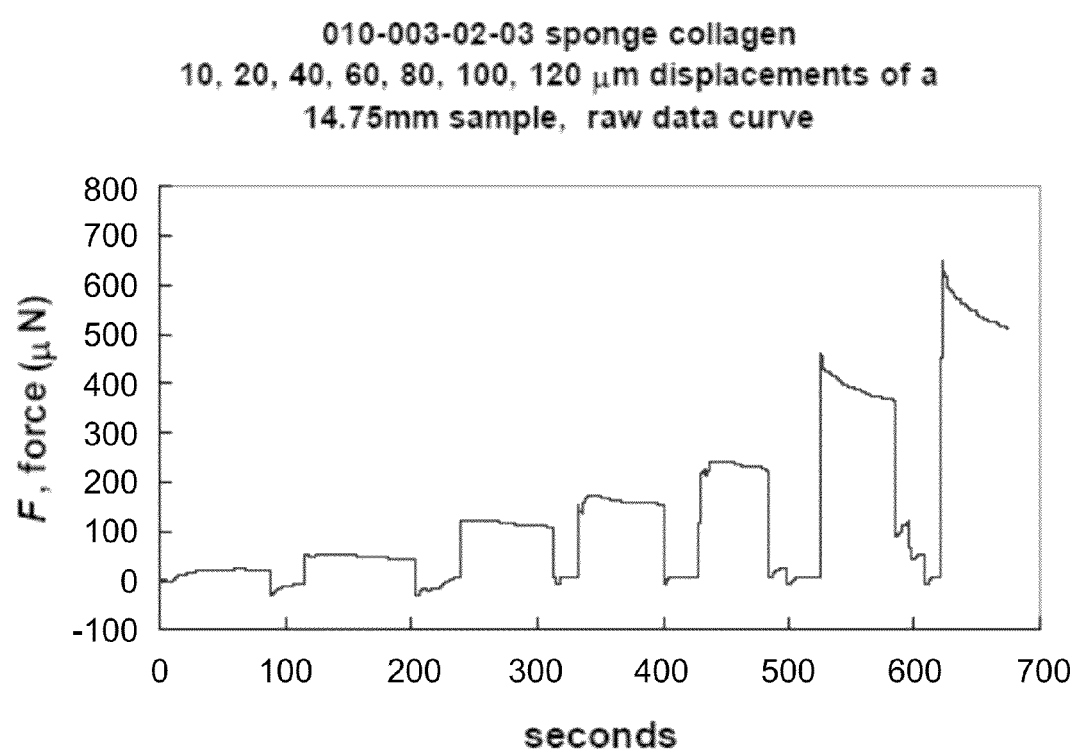

FIG. 8 is a graph illustrating raw force-time data for a collagen sample of the present invention.

Figure 9:
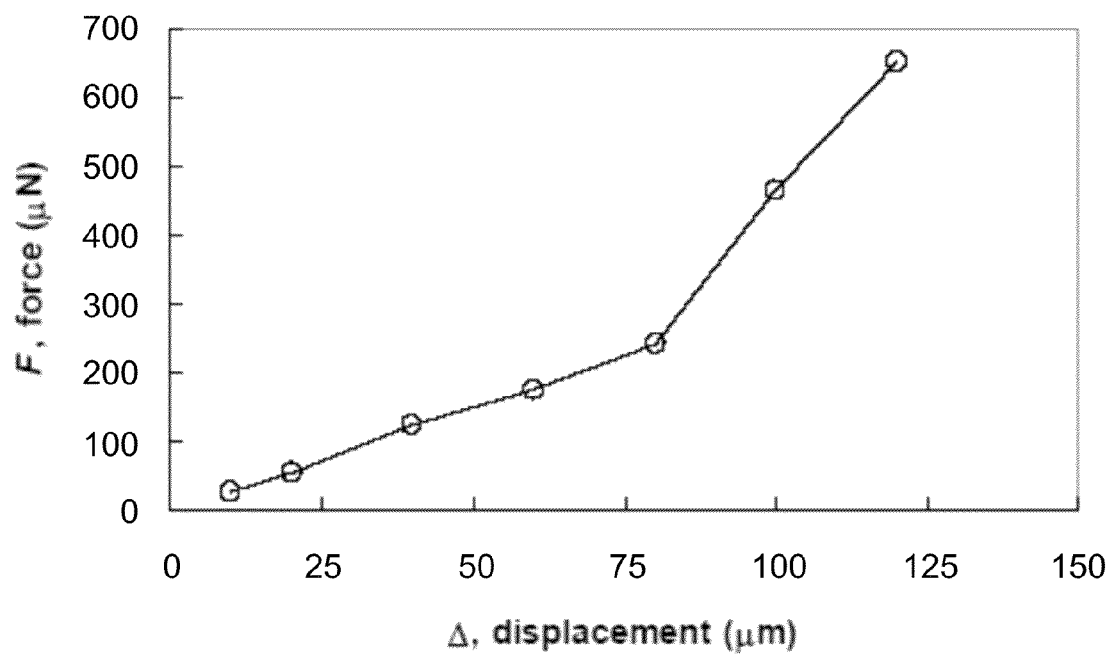

FIG. 9 is graph illustrating force displacement data for a collagen sample of the present invention.

Figure 10:
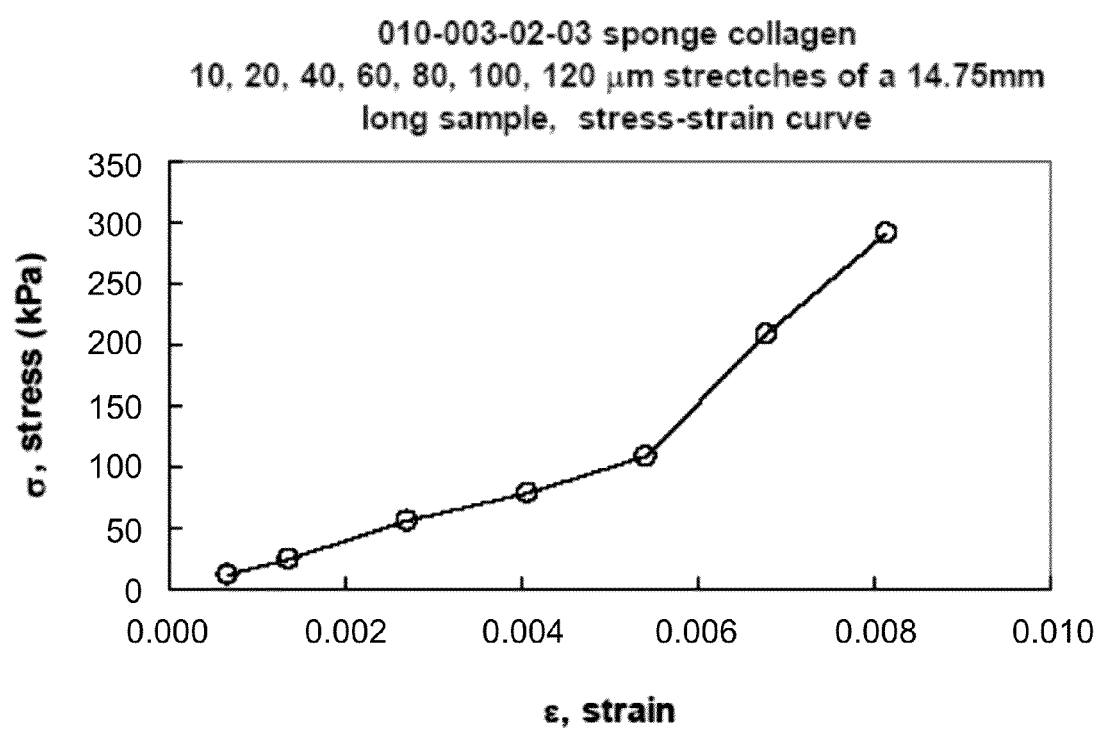

FIG. 10 is a stress-strain curve obtained from force-displacement data.

FIG. 11 is a table illustrating amino acid normalization results for a sample of the collagen of the present invention.

FIG. 12 is a table illustrating amino acid normalization results for a sample of the collagen of the present invention.

FIGS. 13A-B is a read-out of MALDI MS analysis of 1 pmol of sample 1 of the collagen of the present invention.

FIGS. 14A-B is a read-out of MALDI MS analysis of 1 pmol of sample 1 of the collagen of the present invention.

Figure 15A:
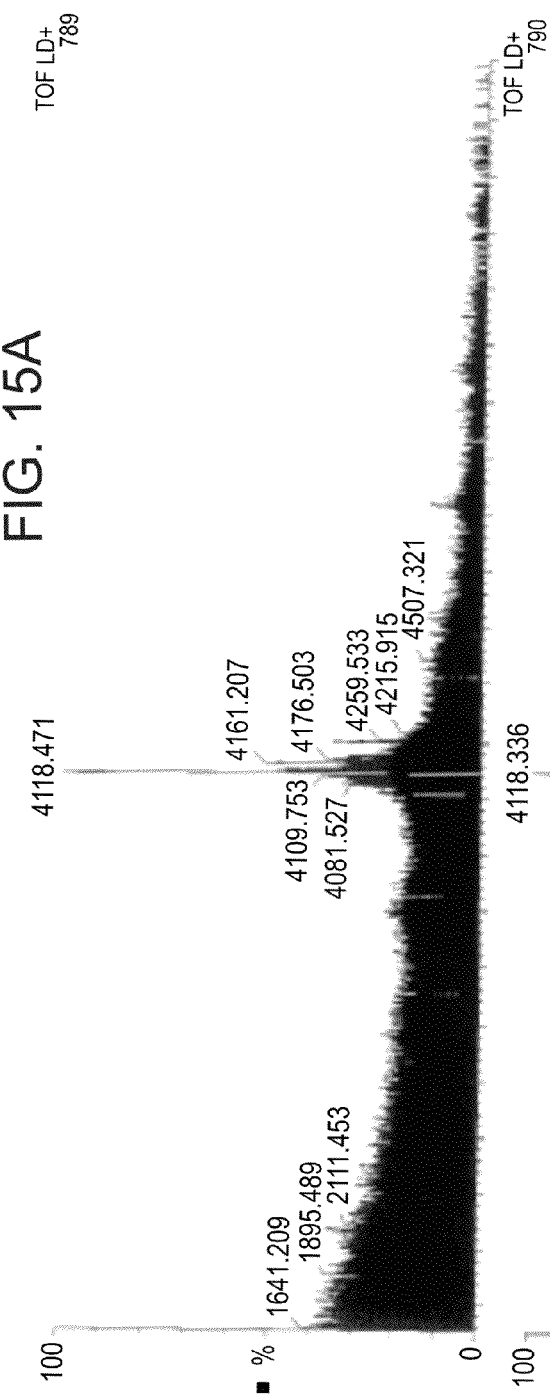
Figure 15B:
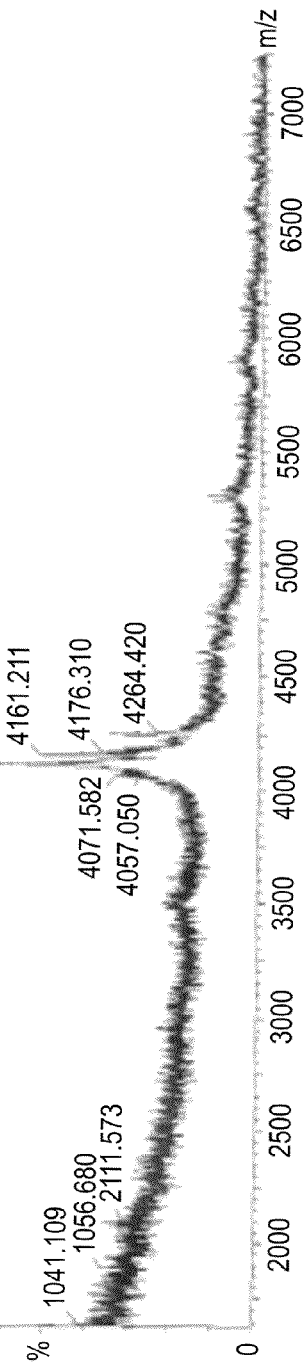

FIGS. 15A-B is a read-out of MALDI MS analysis of 1 pmol of sample 2 of the collagen of the present invention.

FIGS. 16A-B is a read-out of MALDI MS analysis of 1 pmol of sample 2 of the collagen of the present invention.

FIG. 17 is a diagram of the loading profile of an experiment described herein.

Figure 18:
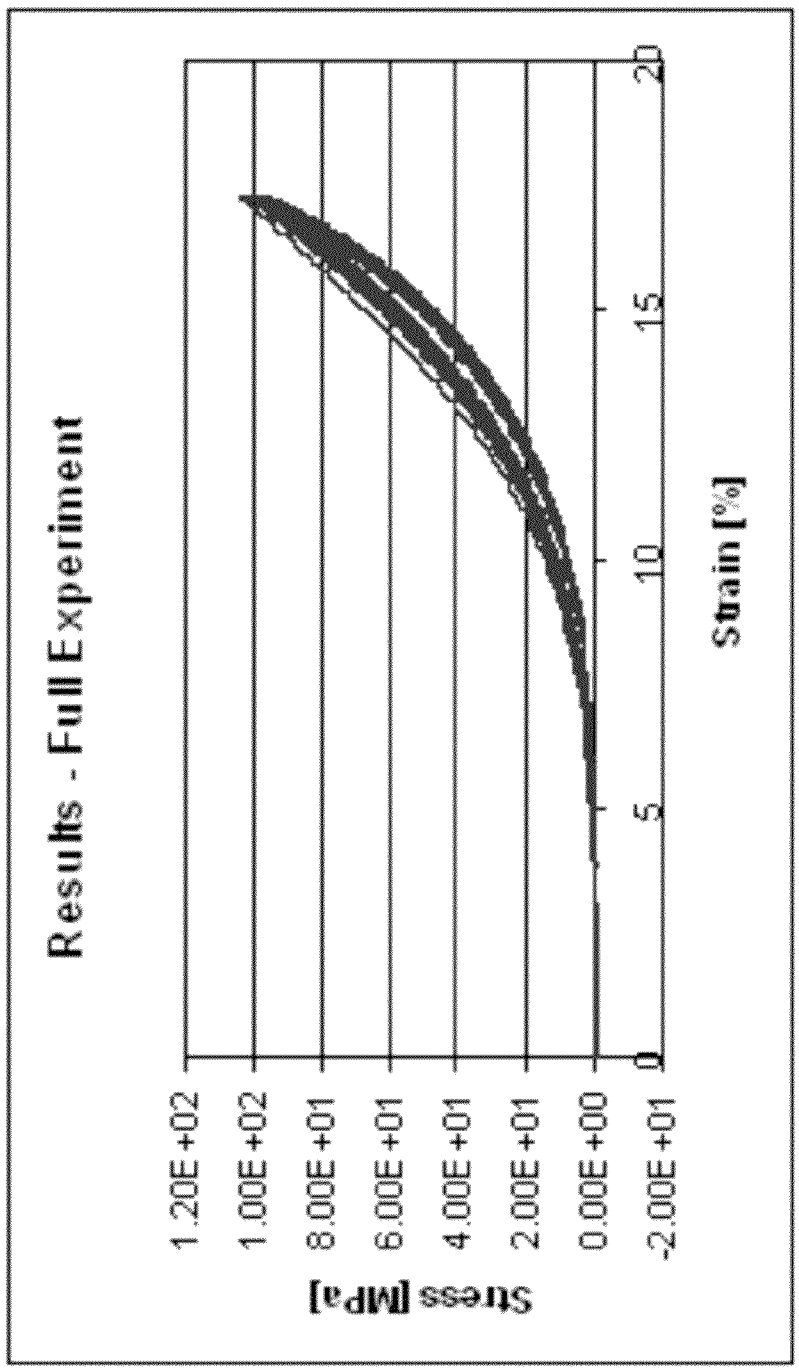

FIG. 18 is a stress-strain curve of the full experiment, loading profile A.

Figure 19:
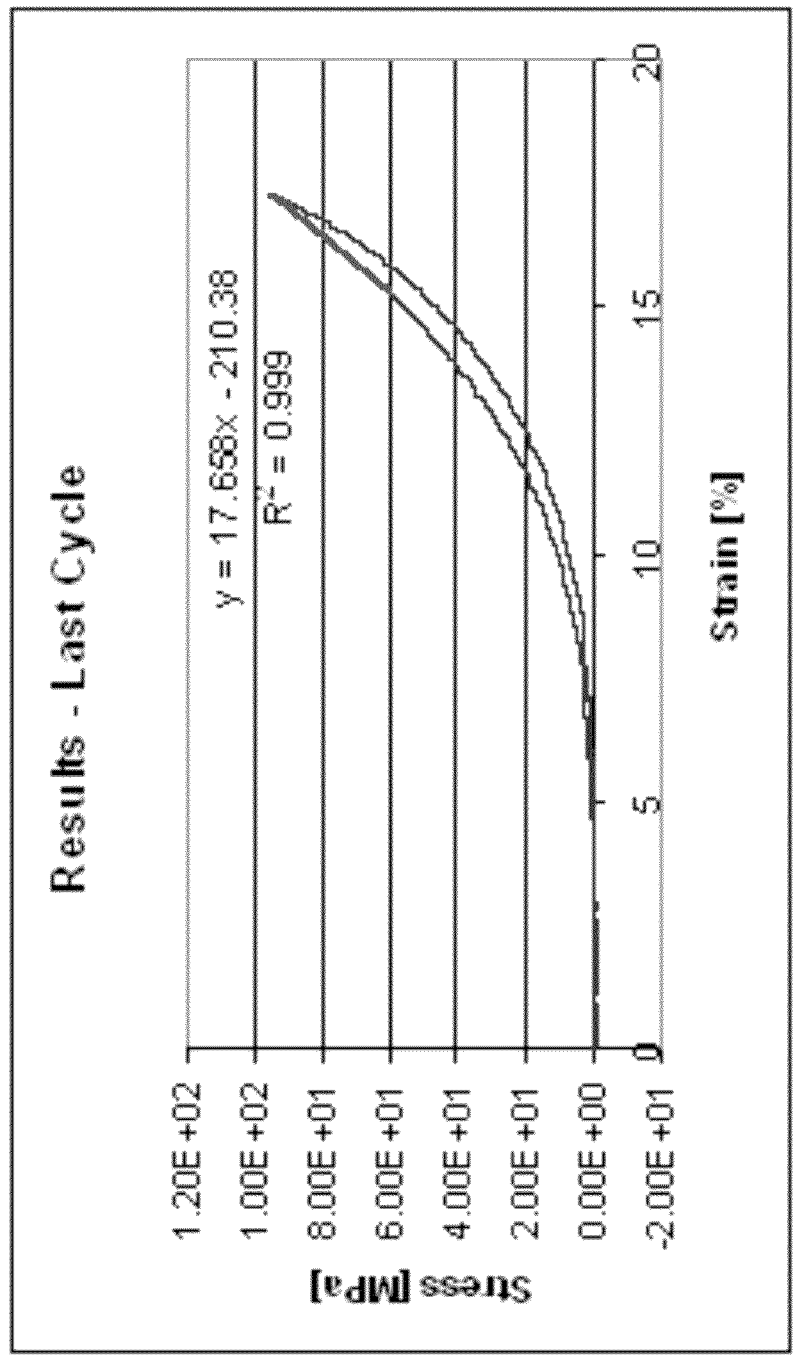

FIG. 19 is a stress-strain curve of the final cycle, loading profile A.

Figure 20:
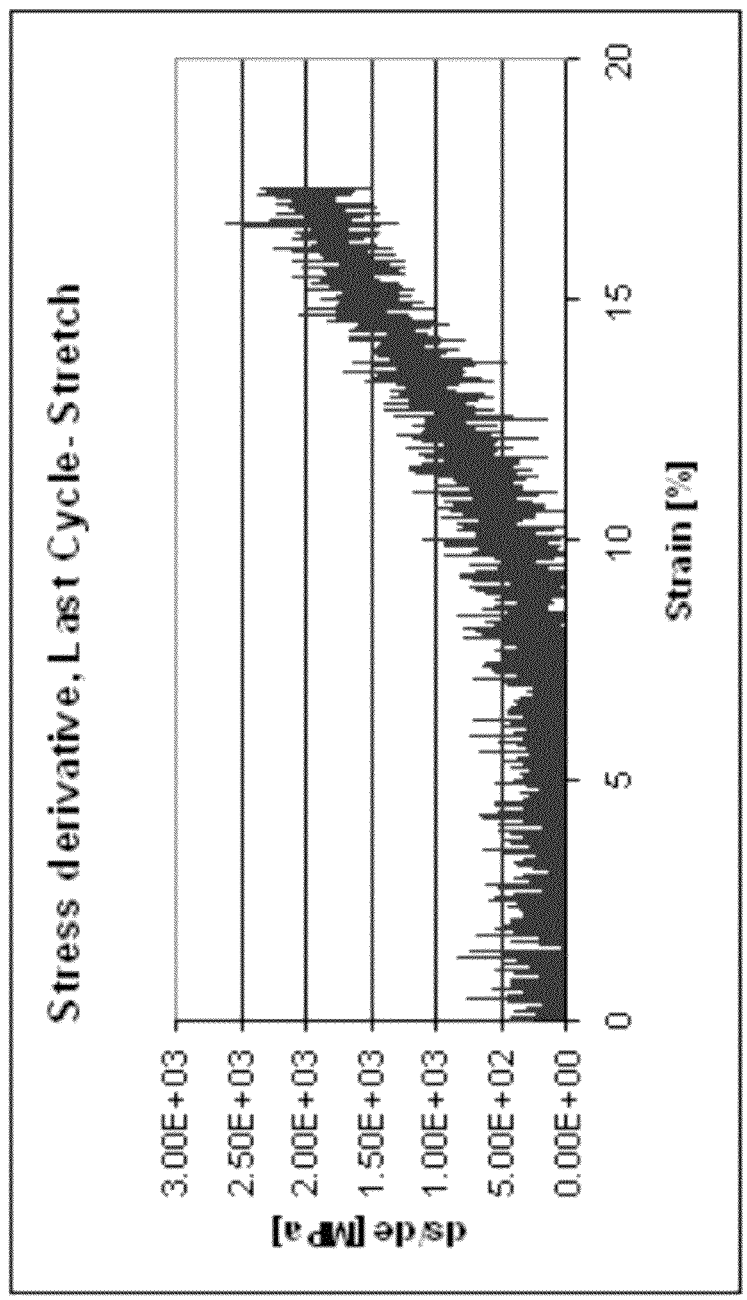

FIG. 20 is a derivative of the stress-strain curve of the last cycle, loading profile A.

Figure 21:
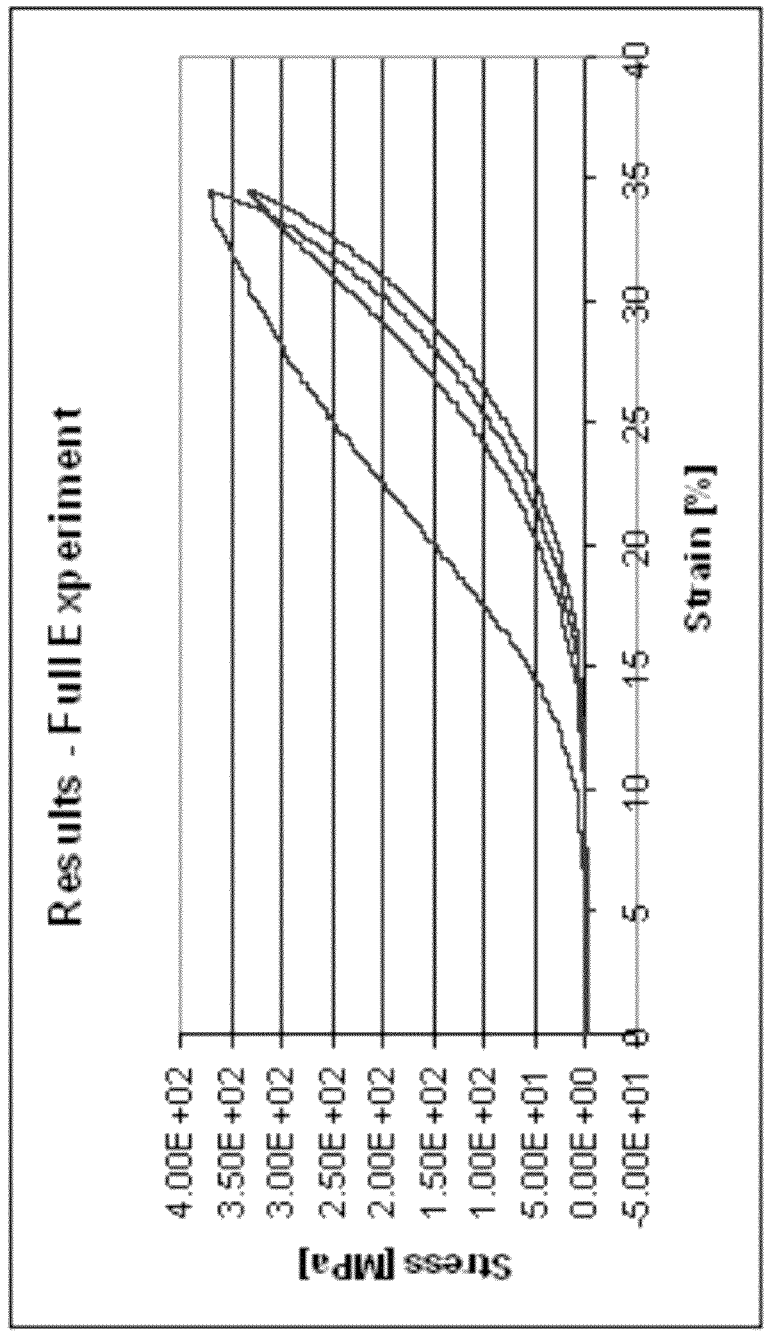

FIG. 21 is a stress-strain curve of the full experiment, loading profile B.

Figure 22:
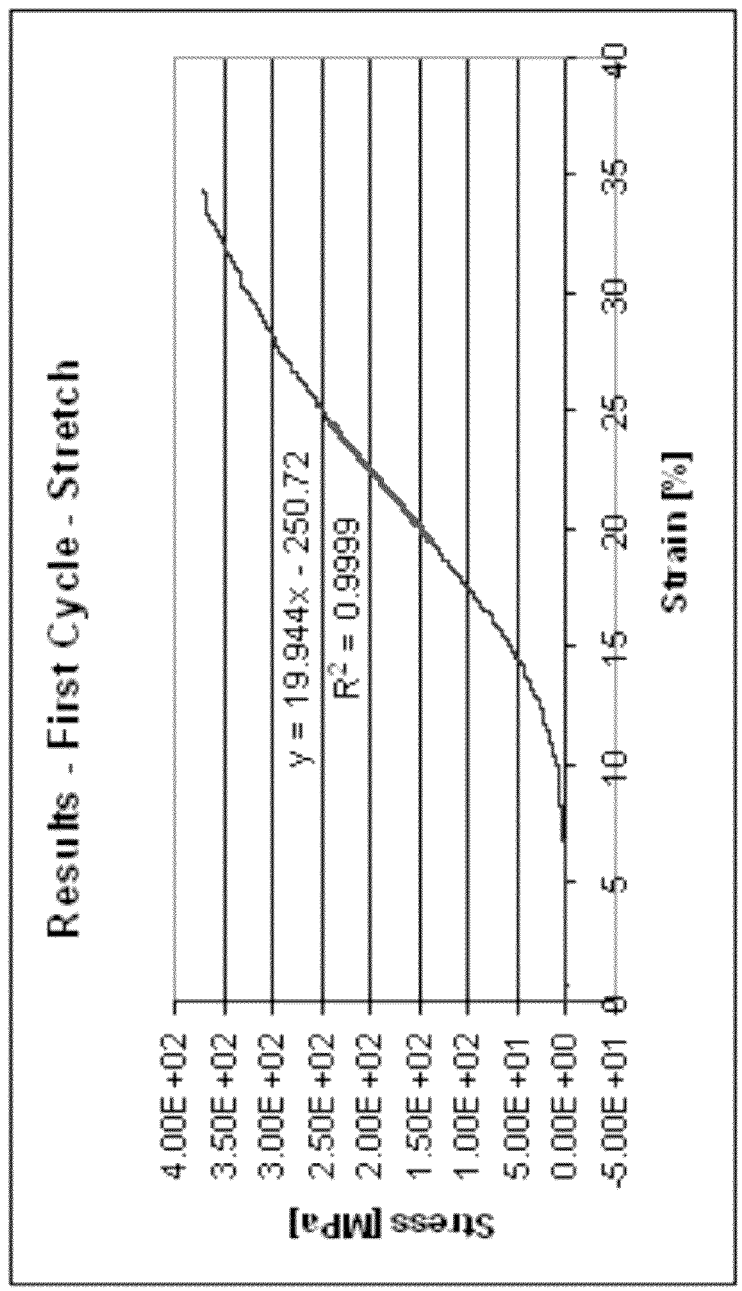

FIG. 22 is a stress-strain curve of the stretch at the first cycle, loading profile B.

Figure 23:
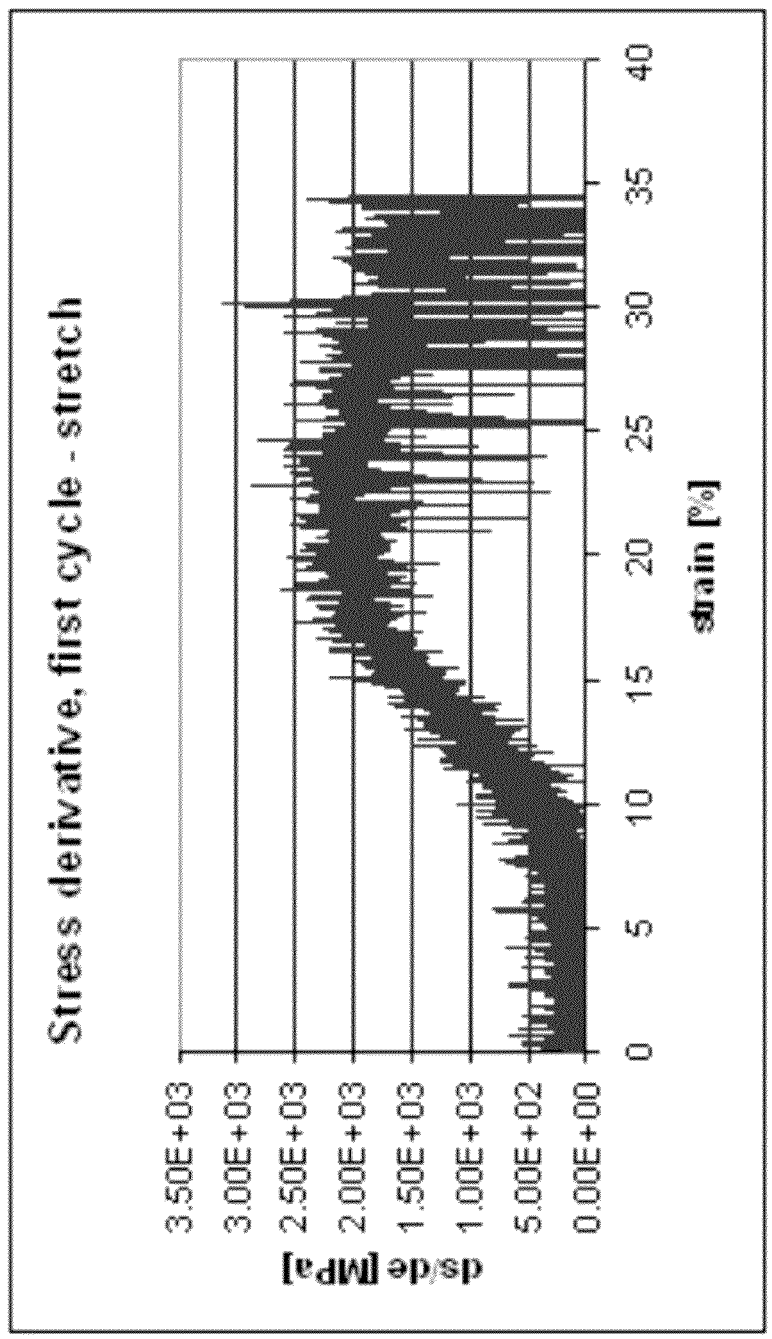

FIG. 23 is a derivative of the stress-strain curve of the stretch at the first cycle, loading profile B.

Figure 24:
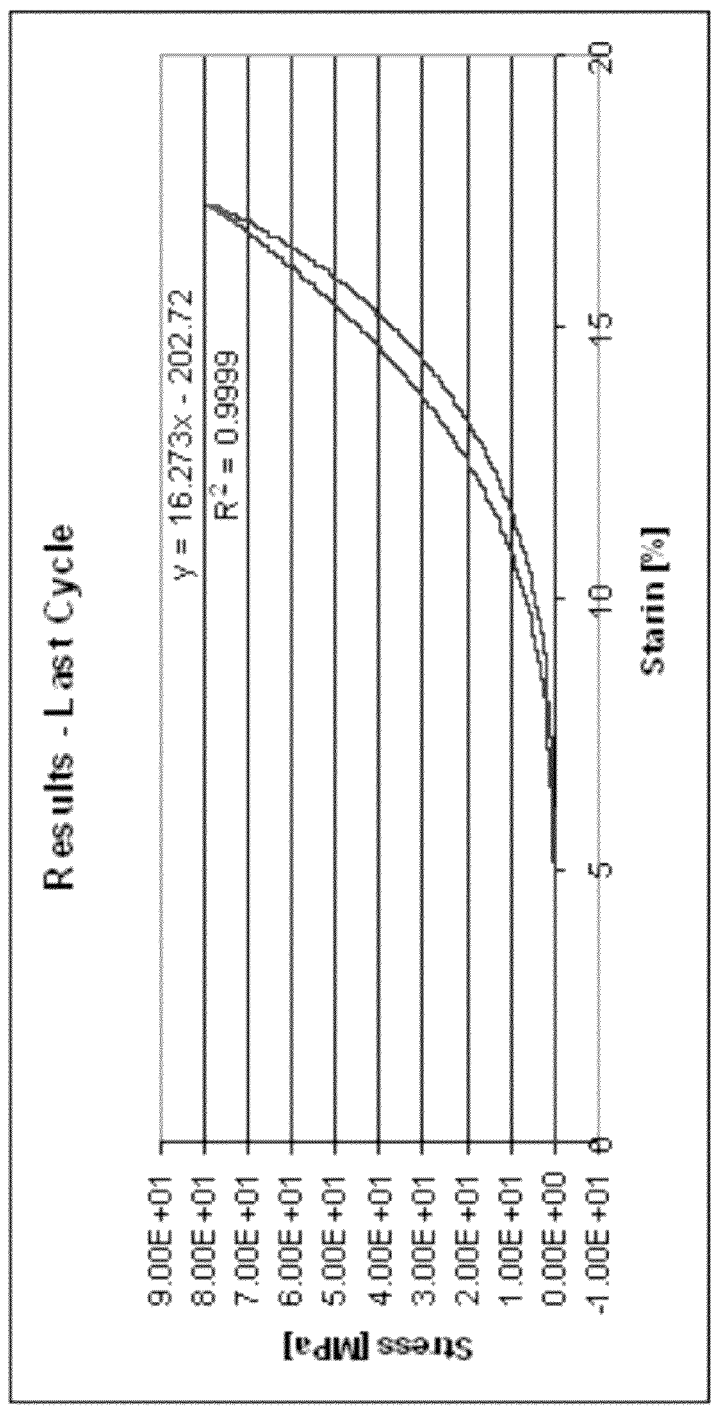

FIG. 24 is a stress-strain curve of the last cycle, loading profile A.

Figure 25:
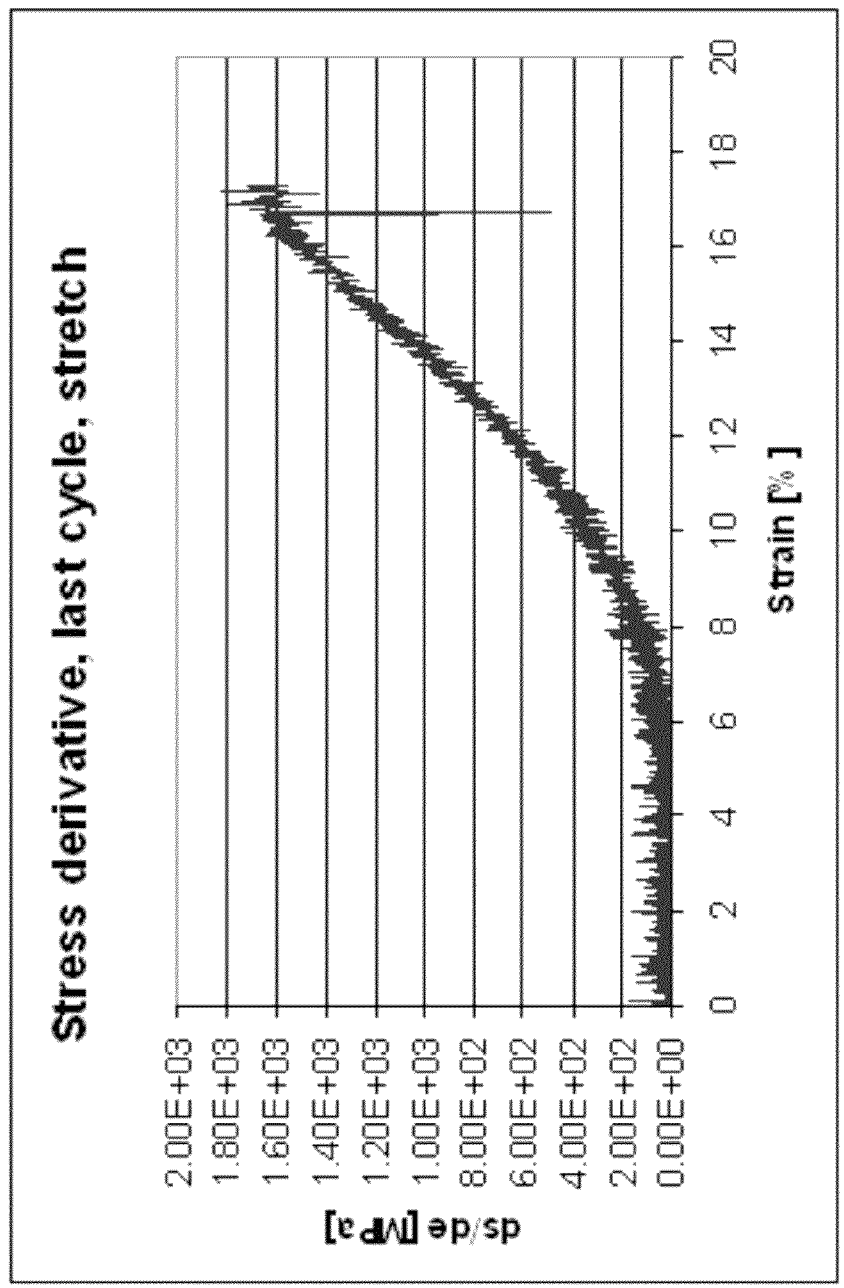

FIG. 25 is a derivative of the stress-strain curve of the last cycle, loading profile A.

Figure 26:
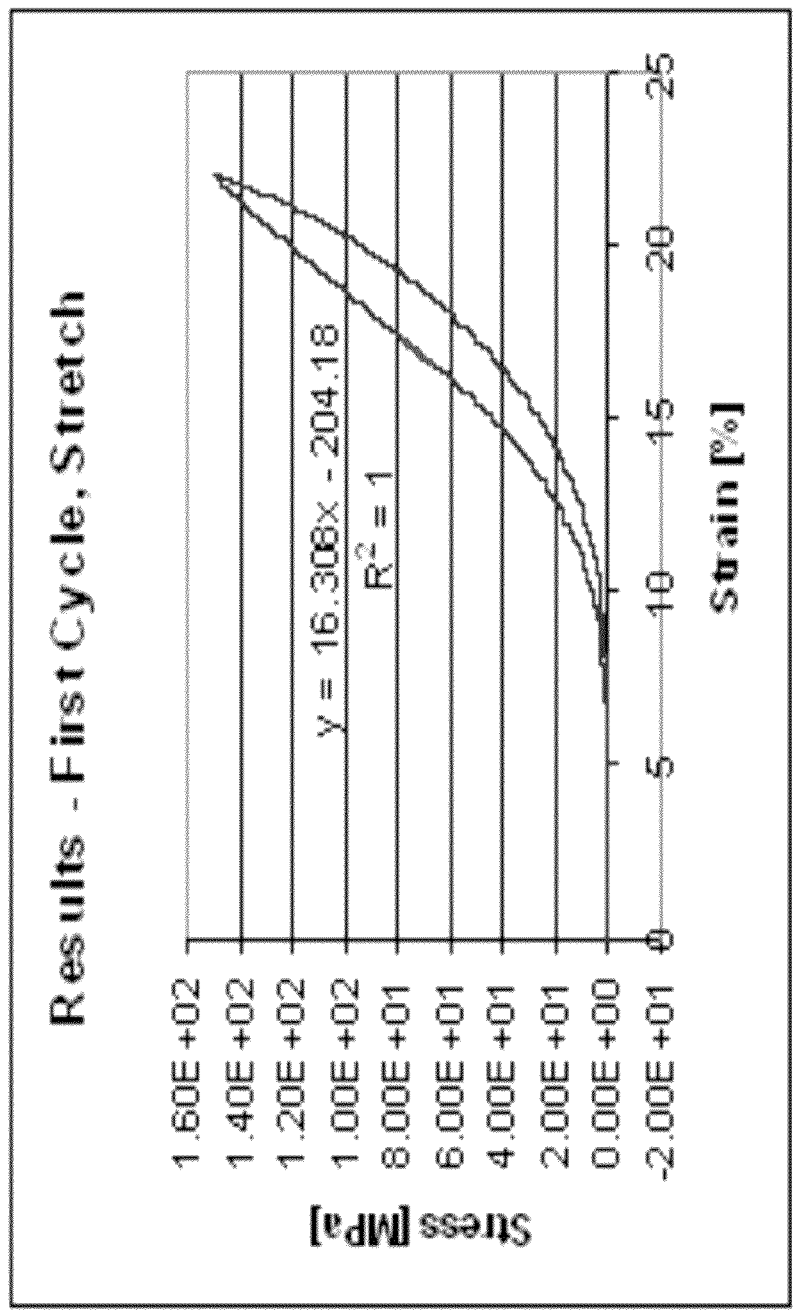

FIG. 26 is a stress-strain curve of the stretch at the first cycle, loading profile B.

Figure 27:
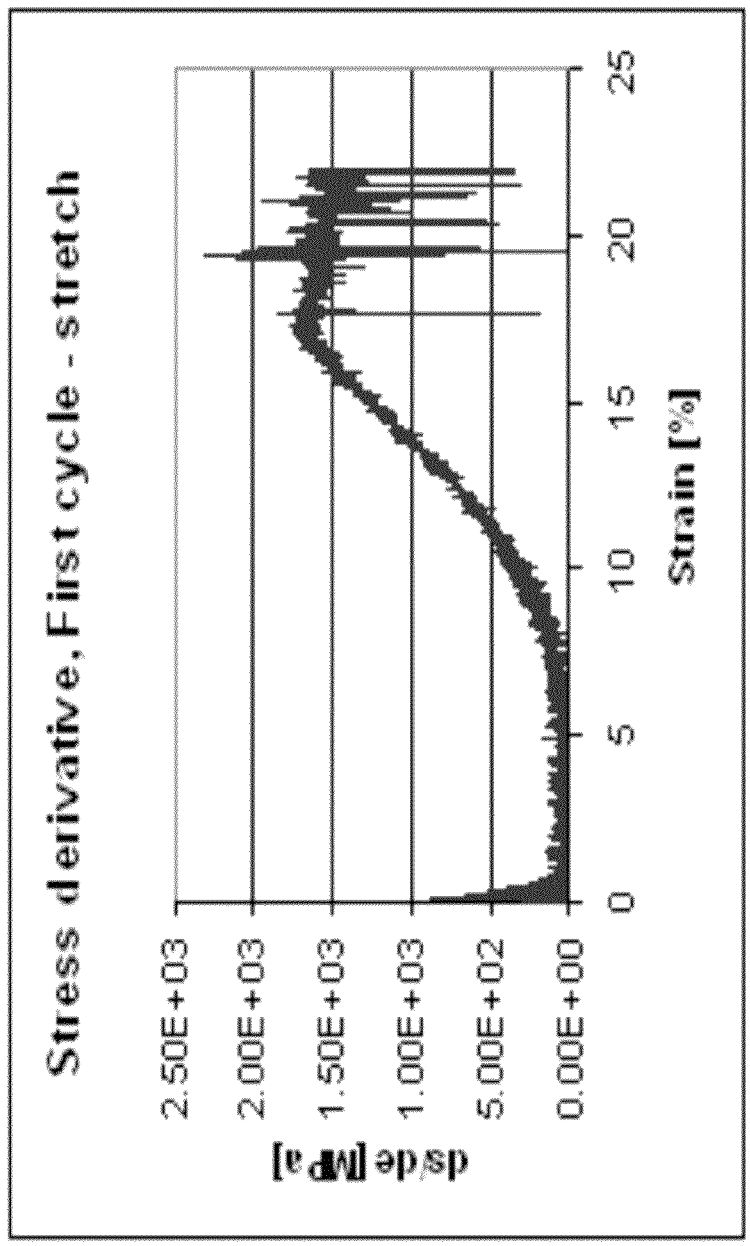
Figure 28B:
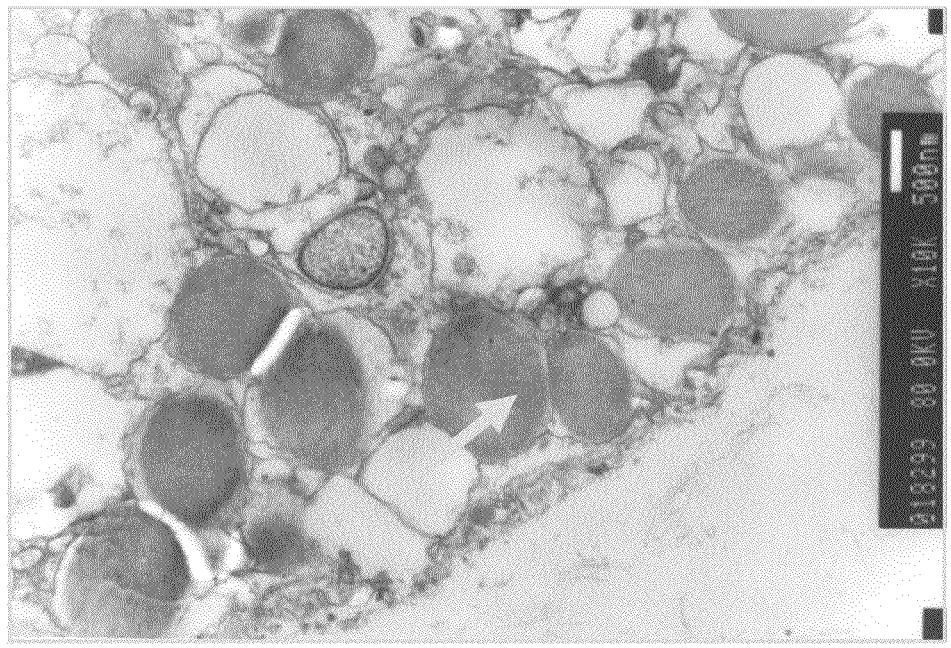
Figure 28A:
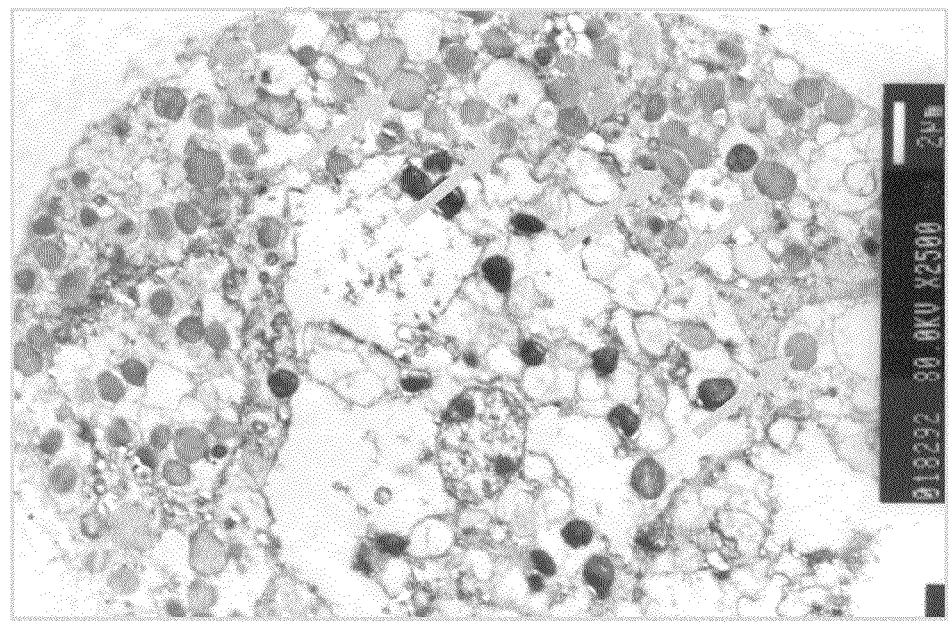
Figure 28D:
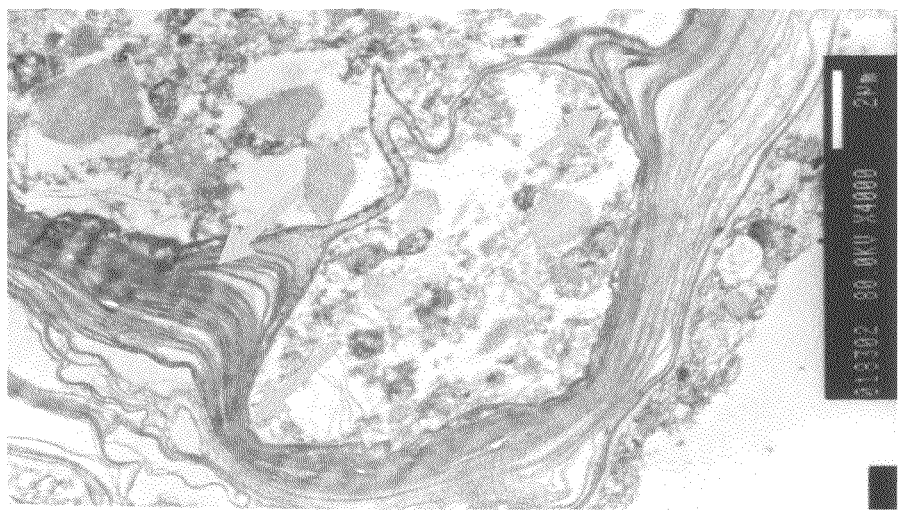
Figure 28C:
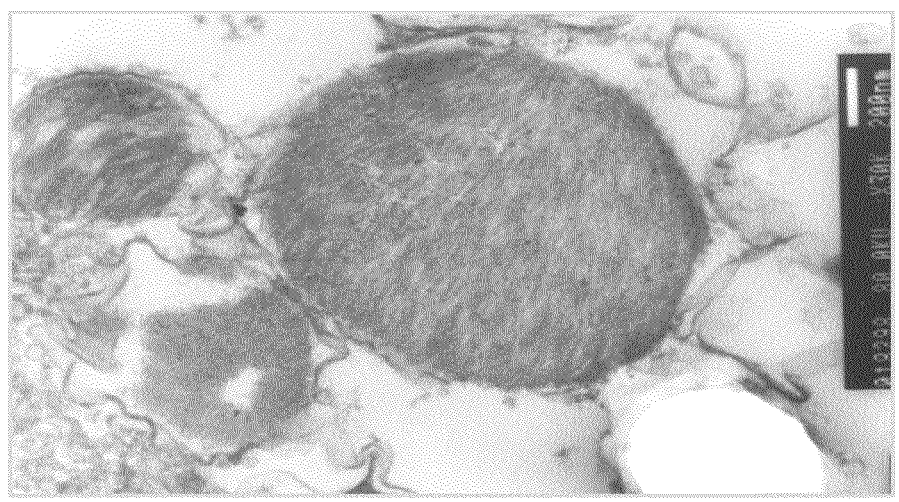
Figures 29A, 29B:
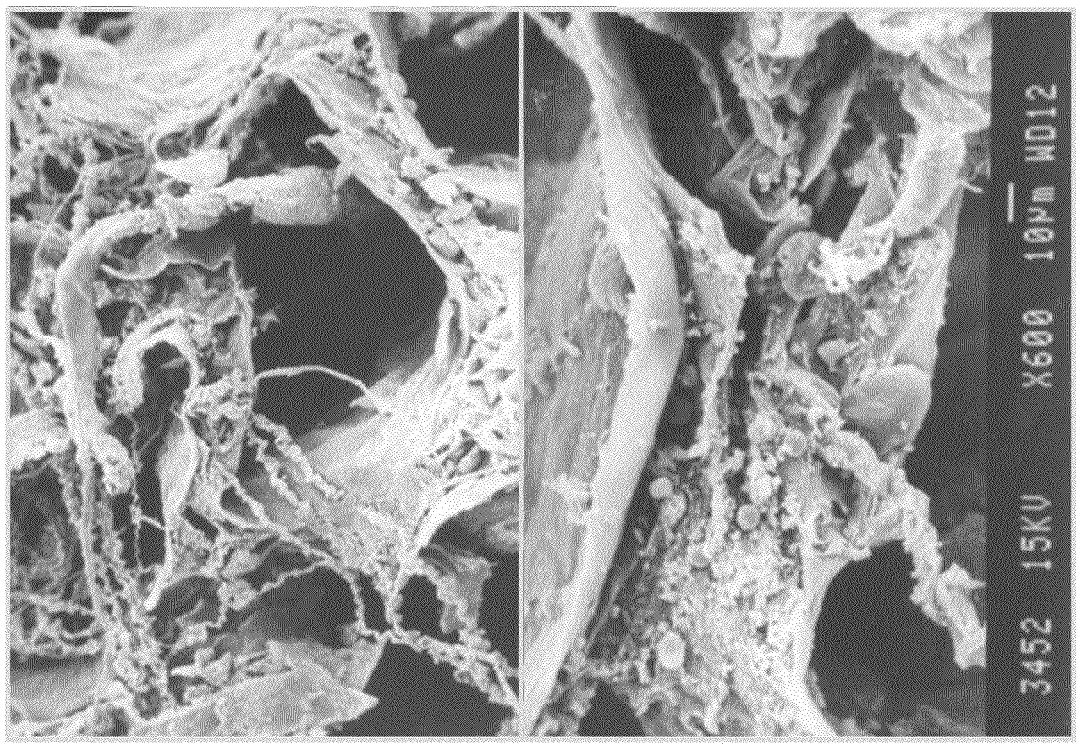
Figure 29C:
Figure 29D:
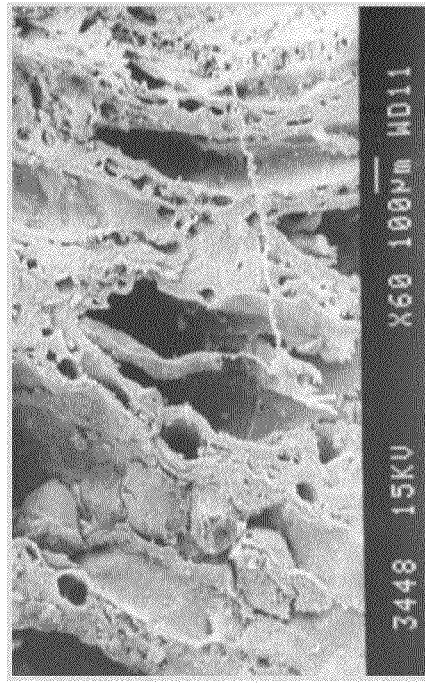

FIG. 27 is a derivative of the stress-strain curve of the stretch at the first cycle, loading profile B.

FIG. 28A-D are electron transmission micrographs of *Sarcophyton* soft coral tissue. A. Cluster of cells within the coenenchyme with organelles where most probably biosynthesis of the collagen fibers takes place (arrows); B. Higher magnification of the vesicles; C. collagen producing vesicle with fibers; D. Collagen fibers surrounding a sclerite (skeletal element) of the soft coral (arrows).

FIGS. 29A-D are scanning electron micrographs of *Sarcophyton* soft coral. A, B. Fibers emerging from the coenenchyme (arrows); C, D. High magnification of helical collagen fibers.

Figure 30B:
Figure 30A:
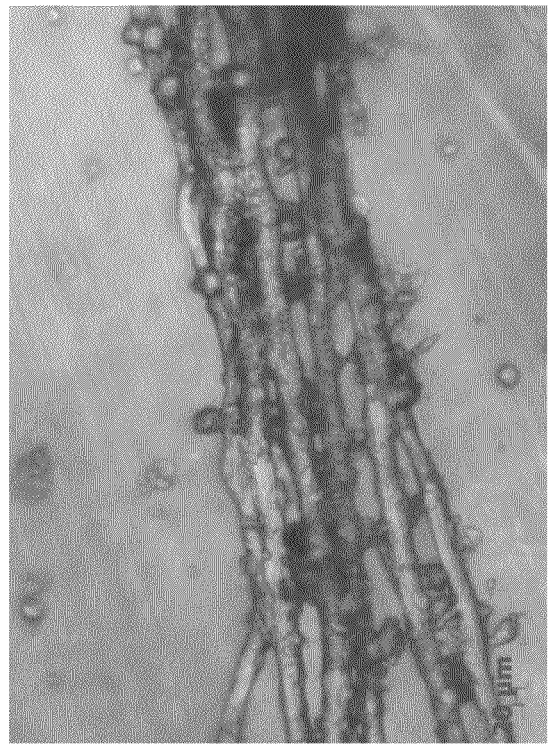

FIG. 30A is a general light microscopy image of the collagen of the present invention.

Figure 30C:

FIGS. 30B-C are scanning electron micrographs of a preosteogenic MBA-15 cell adhering to the fiber in a resting phase (FIG. 30B and undergoing mitotic division (FIG. 30C).

FIGS. 31A-B are photographs of histological sections of preosteogenic cells grown on the soft coral collagen fibers in vivo. The collagen fibers are marked by (C). New fibrous tissue with areas of higher matrix content were formed (circle). No inflammatory cells were visualized.

Figure 32B:
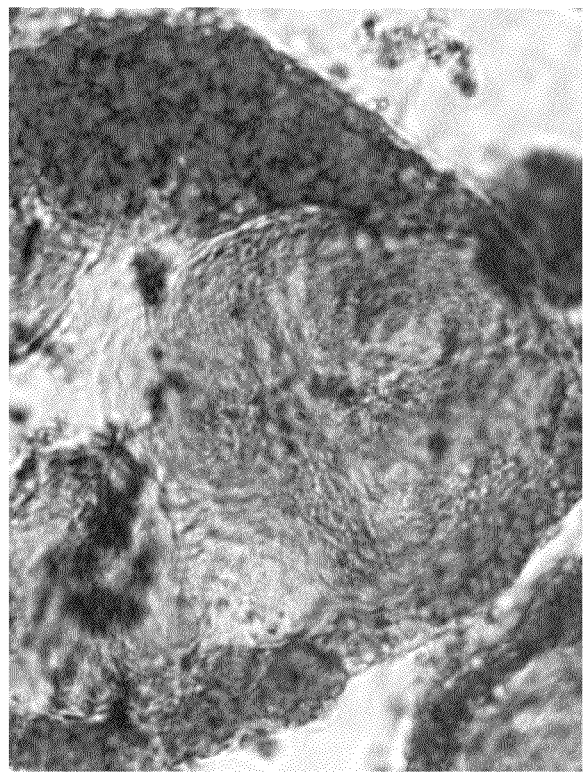
Figure 32A:
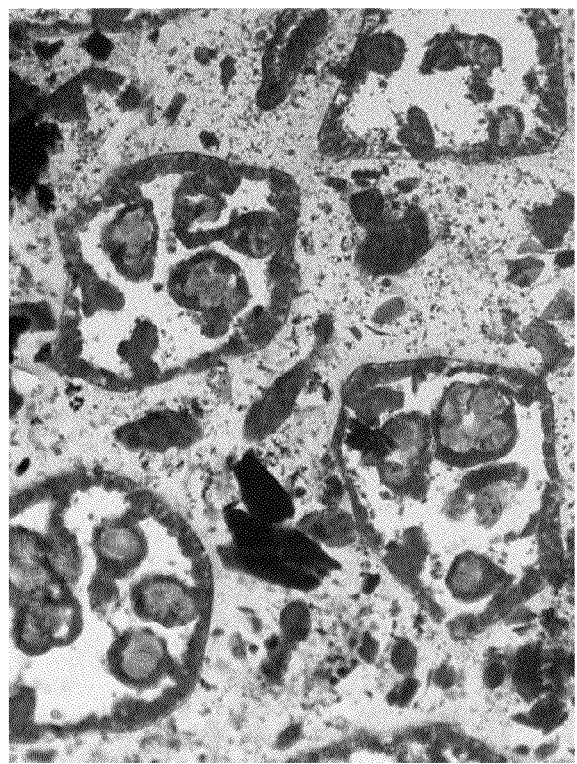

FIGS. 32A-B are photographs of histological sections of *Sarcophyton* sp. treated with collagen specific staining Masson Blue. (A) Assemblages of fibers stained in blue, located in the mesoglea (the non-cellular part of the soft coral) of polyp mesenteries which run along the polyp cavities (×100). (B) Arrangement of the fibers within the mesentery (×400).

Figure 33B:
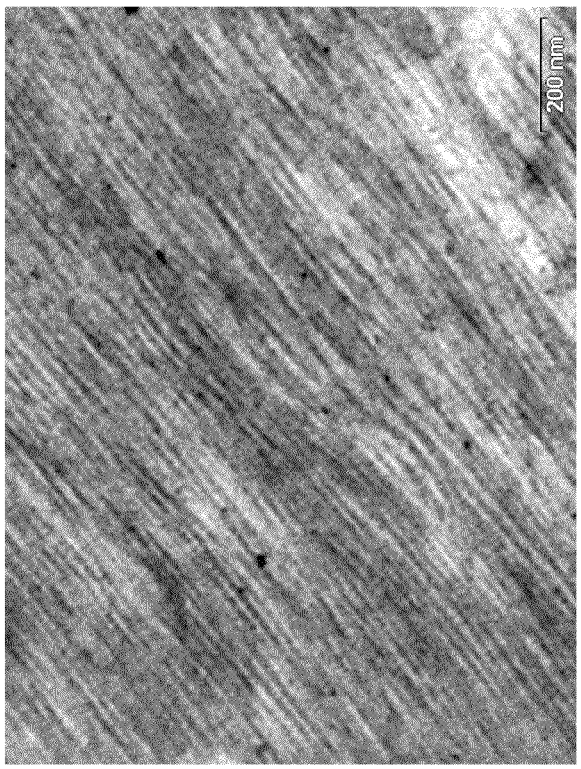
Figure 33A:

FIGS. 33A-B are transmission electron micrographs of collagen fibers of *Sarcophyton* sp. revealing the fibrils. FIG. 33B (Nikon, 100×10, oil immersion) is a magnification of FIG. 33A (Nikon, 40×10, oil immersion).

Figure 34:

FIG. 34 is a transmission electron micrograph of negatively stained fibrils that were detached from the fiber by sonication.

Figure 35:
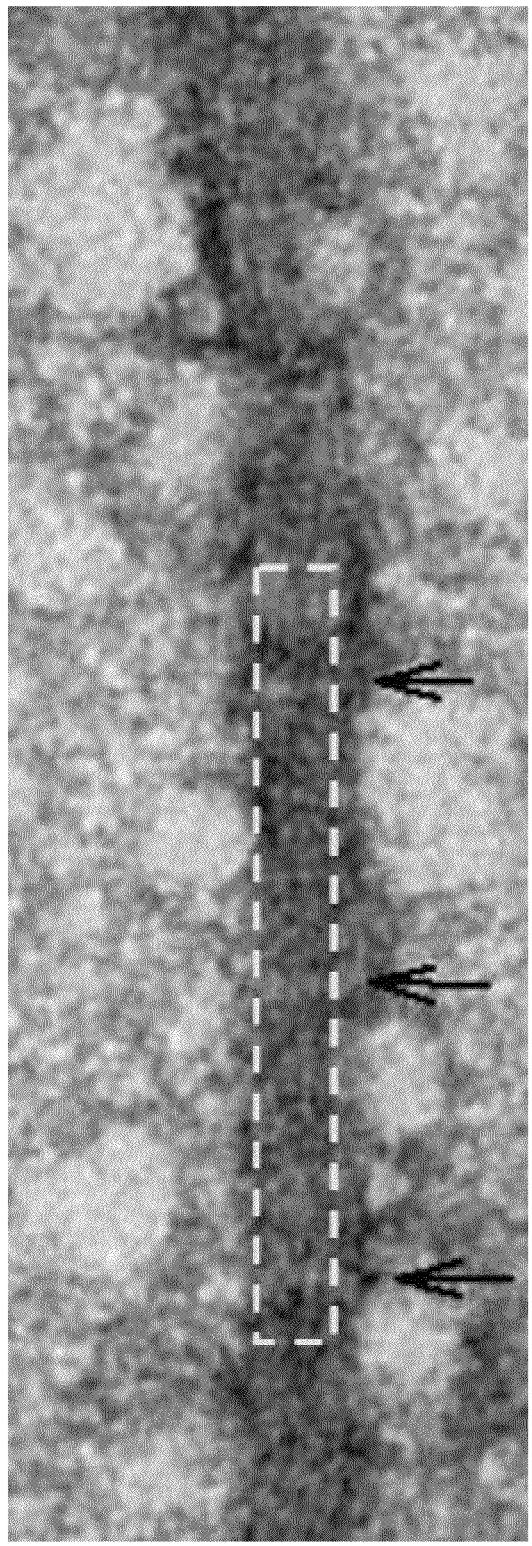

FIG. 35 is a transmission electron micrograph of a fibril of the soft coral collagen aligned horizontally by Image-J. The yellow marked rectangular is placed over an area and intensity histogram was conducted. Image-J averaged the values in the vertical direction at all points along the horizontal direction and provided an average intensity distribution along the collagen fibril. The major bands are at ca 70 nm, but there is some lower amplitude banding inside this 70 nm unit as expected from negatively stained collagen.

Figure 36:

FIG. 36 is a light microscopy image of the fibers according to an embodiment of the present invention (×100, oil immersion).

Figure 37:
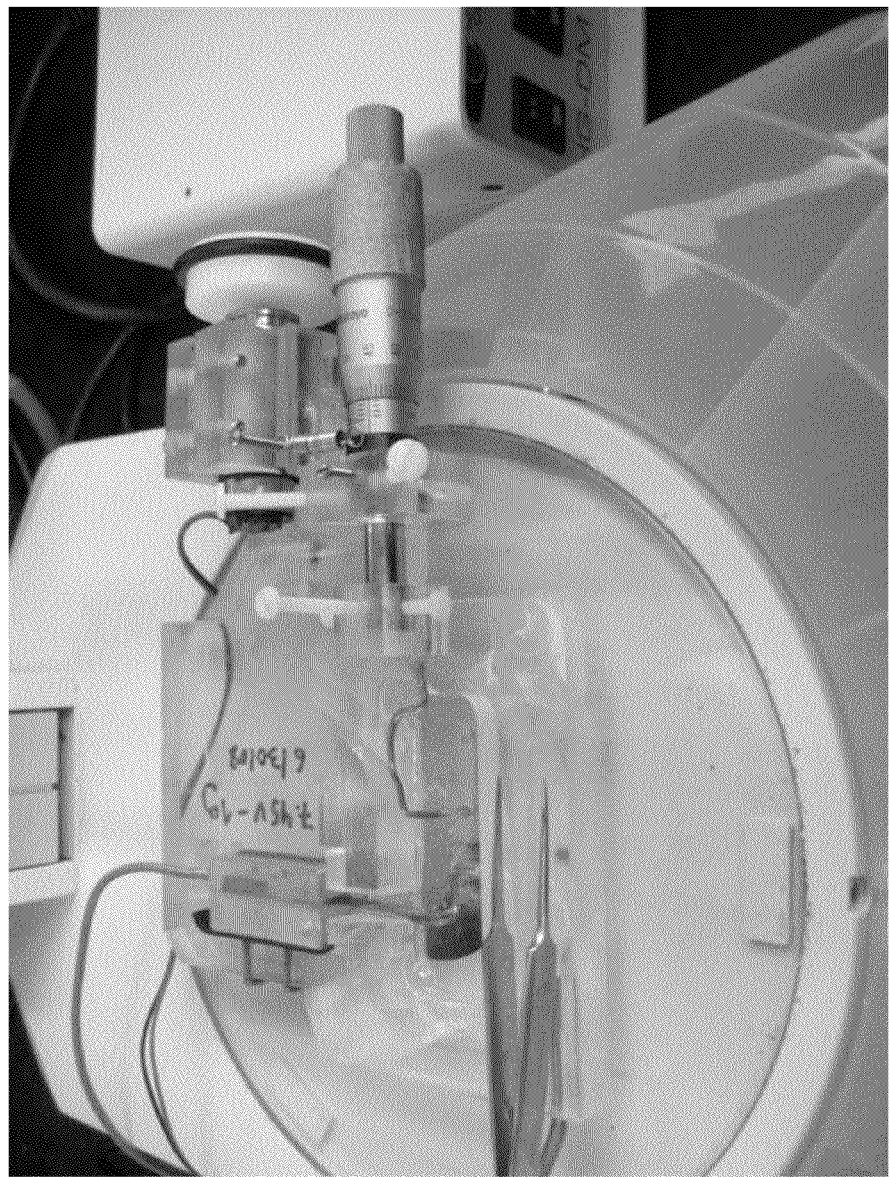

FIG. 37 is a photograph of a tensometer installed on the dissecting microscope for analyzing the collagen fibers isolated from the mesoglea of the soft coral *Sarcophyton* sp.

Figure 38:
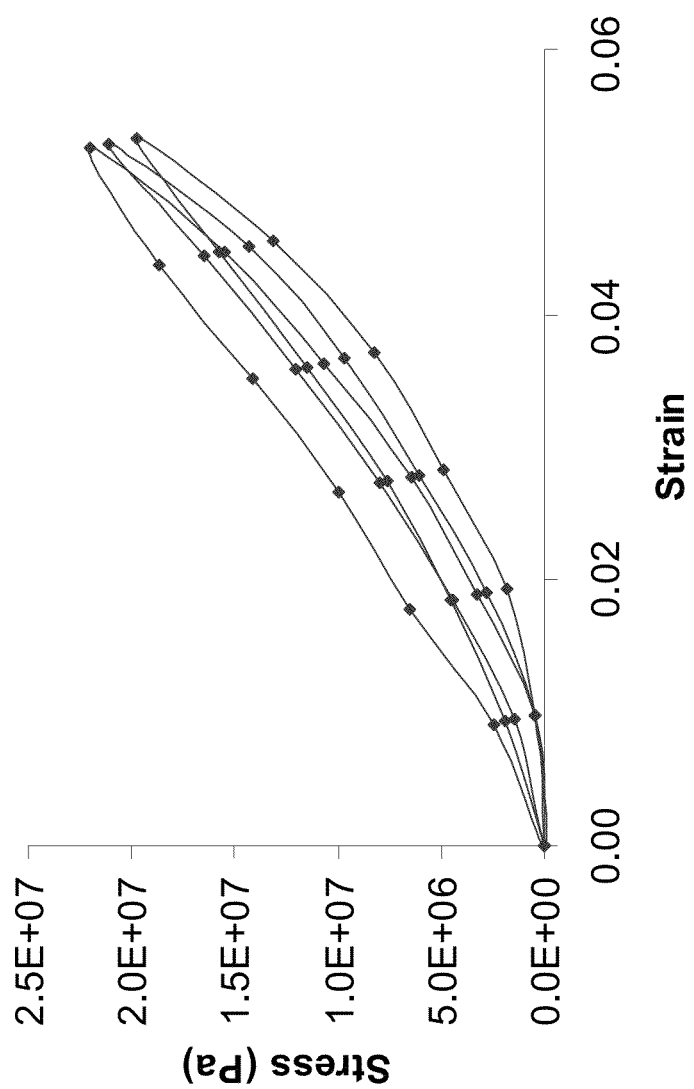

FIG. 38 is a graph of a representative stress-strain curve of a preconditioning cycle of the collagen fibers isolated from the mesoglea of the soft coral *Sarcophyton* sp.

Figure 39:
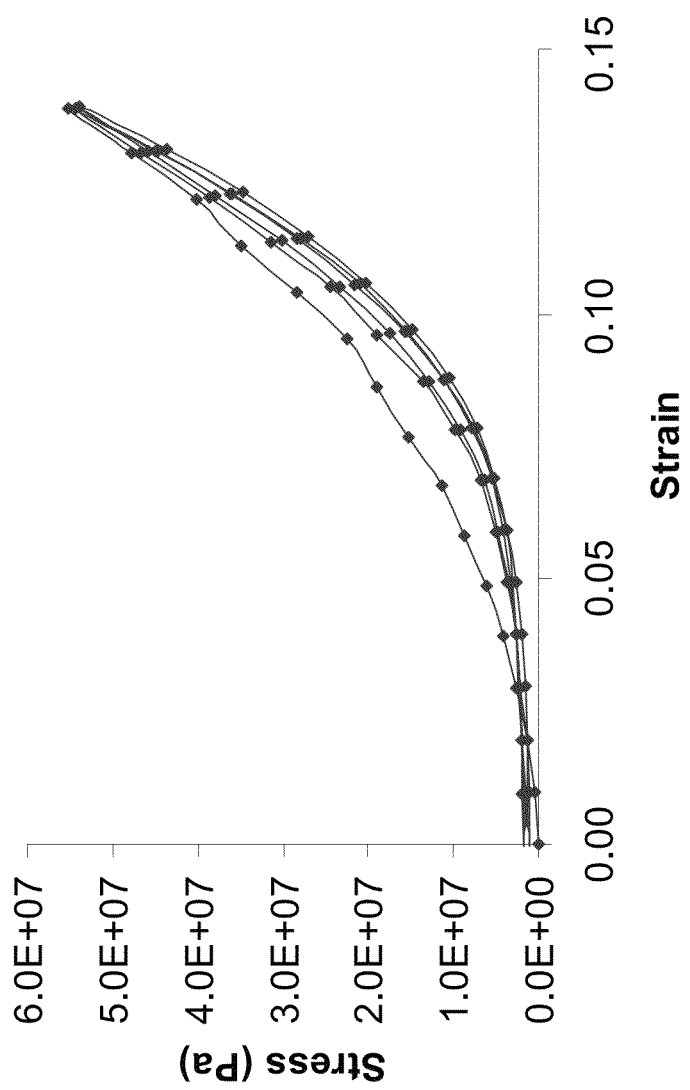

FIG. 39 is a representative stress-strain curve of loading-unloading cycle (E=0.9 GPa) of the collagen fibers isolated from the mesoglea of the soft coral *Sarcophyton* sp.

Figure 40:
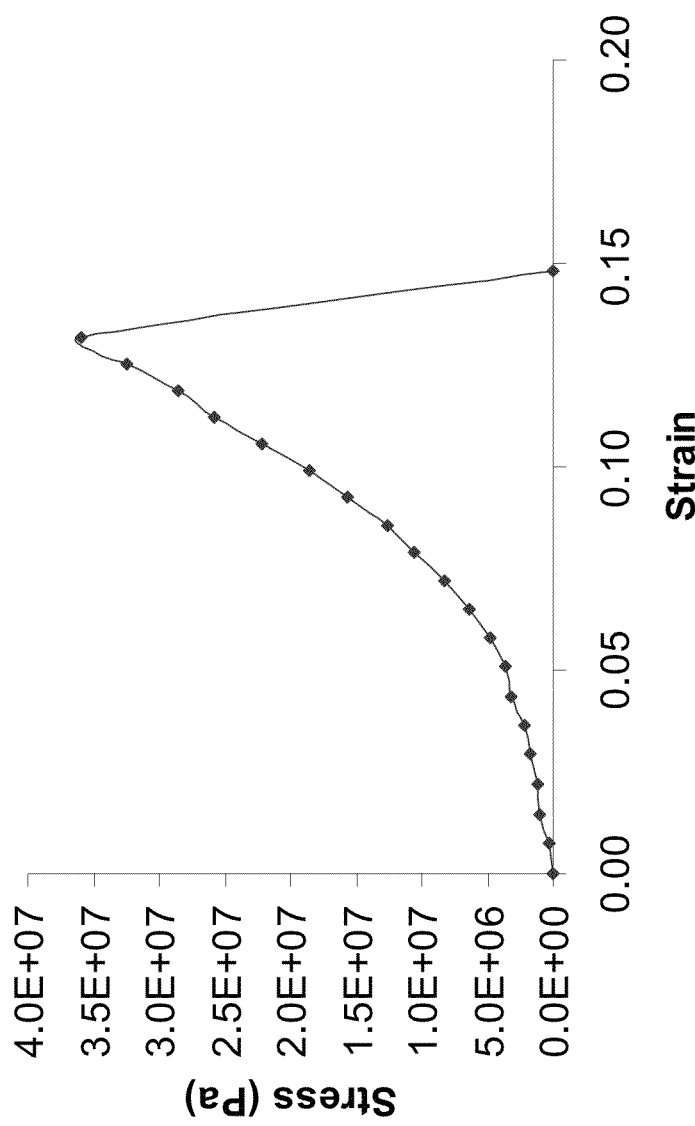

FIG. 40 is a representative stress-strain curve of load to failure of the collagen fibers isolated from the mesoglea of the soft coral *Sarcophyton* sp.

DESCRIPTION OF EMBODIMENTS OF THE INVENTION

The present invention, in some embodiments thereof, relates to a collagen comprising enhanced elasticity and, more particularly, but not exclusively, to a coral-derived collagen.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Collagen is the principal structural protein in the body and constitutes approximately one-third of the total body protein. It comprises most of the organic matter of the skin, tendons, bones and teeth and occurs as fibrous inclusions in most other body structures. Some of the properties of collagen are its high tensile strength; its ion exchanging ability, due in part to the binding of electrolytes, metabolites and drugs; its low antigenicity, due to masking of potential antigenic determinants by the helical structure, and its low extensibility, semipermeability, and solubility. Furthermore collagen is a natural substance for cell adhesion. These properties make this protein suitable for fabrication of bioremodelable research products and medical devices such as implantable prostheses, cell growth substrates, and cellular and a-cellular tissue constructs.

During an underwater excursion on the shores of the Red Sea, the present inventors identified a coral comprising long fibrous extensions. Following extraction and analysis of these fibers, the present inventors identified that they comprise a novel form of collagen. Mechanical testing showed that the fibers comprised a unique combination of properties being both highly elastic and comprising a high mechanical strength (FIGS. 8-10 and 18-27).

Specifically, the coral fibers were shown to have a high reversible extensibility compared with mammalian collagen fibers (e.g., the coral fibers could be reversibly stretched to strains 2-3 fold greater than mammalian collagen fibers). Furthermore, the stiffness of the coral fibers was shown to be at the top range of the reported stiffness range for mammalian collagen fibers.

Whilst further reducing the present invention to practice, the present inventors showed that the coral of the present invention could be used as a scaffolding biomaterial for cell growth and tissue regeneration (FIGS. 30A-C). In vivo subcutaneous transplantation of the fibers revealed their immunocompetent nature.

Thus, according to one aspect of the present invention, there is provided an isolated collagen fiber, wherein a length of the fiber prior to stretching by about 15%, is identical to a length of the fiber following the stretching by about 15%.

The term "collagen" as used herein, refers to a polypeptide having a triple helix structure and containing a repeating Gly-X-Y triplet, where X and Y can be any amino acid but are frequently the imino acids proline and hydroxyproline. According to one embodiment, the collagen is a type I, II, III, V, XI, or biologically active fragments therefrom.

As used herein, the phrase "collagen fiber" refers to a non-soluble self-aggregate of the above-mentioned collagen comprising a fibrous structure in which collagen molecules are packed in series and also in parallel.

According to one embodiment, a length of the fiber prior to stretching by about 16%, is identical to a length of the fiber following the stretching by about 16%.

According to another embodiment, a length of the fiber prior to stretching by about 17%, is identical to a length of the fiber following the stretching by about 17%.

According to another embodiment, a length of the fiber prior to stretching by about 18%, is identical to a length of the fiber following the stretching by about 18%.

According to another embodiment, a length of the fiber prior to stretching by about 19%, is identical to a length of the fiber following the stretching by about 19%.

According to another embodiment, a length of the fiber prior to stretching by about 20%, is identical to a length of the fiber following the stretching by about 20%.

According to another embodiment, a length of the fiber prior to stretching by about 21%, is identical to a length of the fiber following the stretching by about 21%.

According to another embodiment, a length of the fiber prior to stretching by about 22%, is identical to a length of the fiber following the stretching by about 22%.

According to another embodiment, a length of the fiber prior to stretching by about 23%, is identical to a length of the fiber following the stretching by about 23%.

According to one embodiment, the collagen of the present invention does not comprise the terminal non-helical regions (telopeptide) existing at both ends of native collagen—i.e. the collagen comprises atelocollagen.

Contemplated organisms from which the collagen of the present invention may be extracted include vertebrate organisms, including mammalian organisms and fish and invertebrate organisms including cnidaria such as jelly fish and coral.

Exemplary coral from which the collagen of the present invention may be extracted include, but are not limited to Hydrocorals, Stony (Hard) Corals, Colonial Anemones & Button Polyps, Mushroom Coral, Sea Pens, Soft Corals, Gorgonians, Stoloniferans.

According to one embodiment, the coral is the soft coral *Sarcophyton* sp.

Although the present invention is exemplified by a native collagen (i.e. one that has not been engineered or modified, it will be appreciated that the present invention also contemplates genetically modified forms of collagen—for example collagenase resistant collagens and the like [Wu et al., Proc Natl. Acad Sci, Vol. 87, p. 5888-5892, 1990] and other forms of manufactured collagen.

Figure 1:
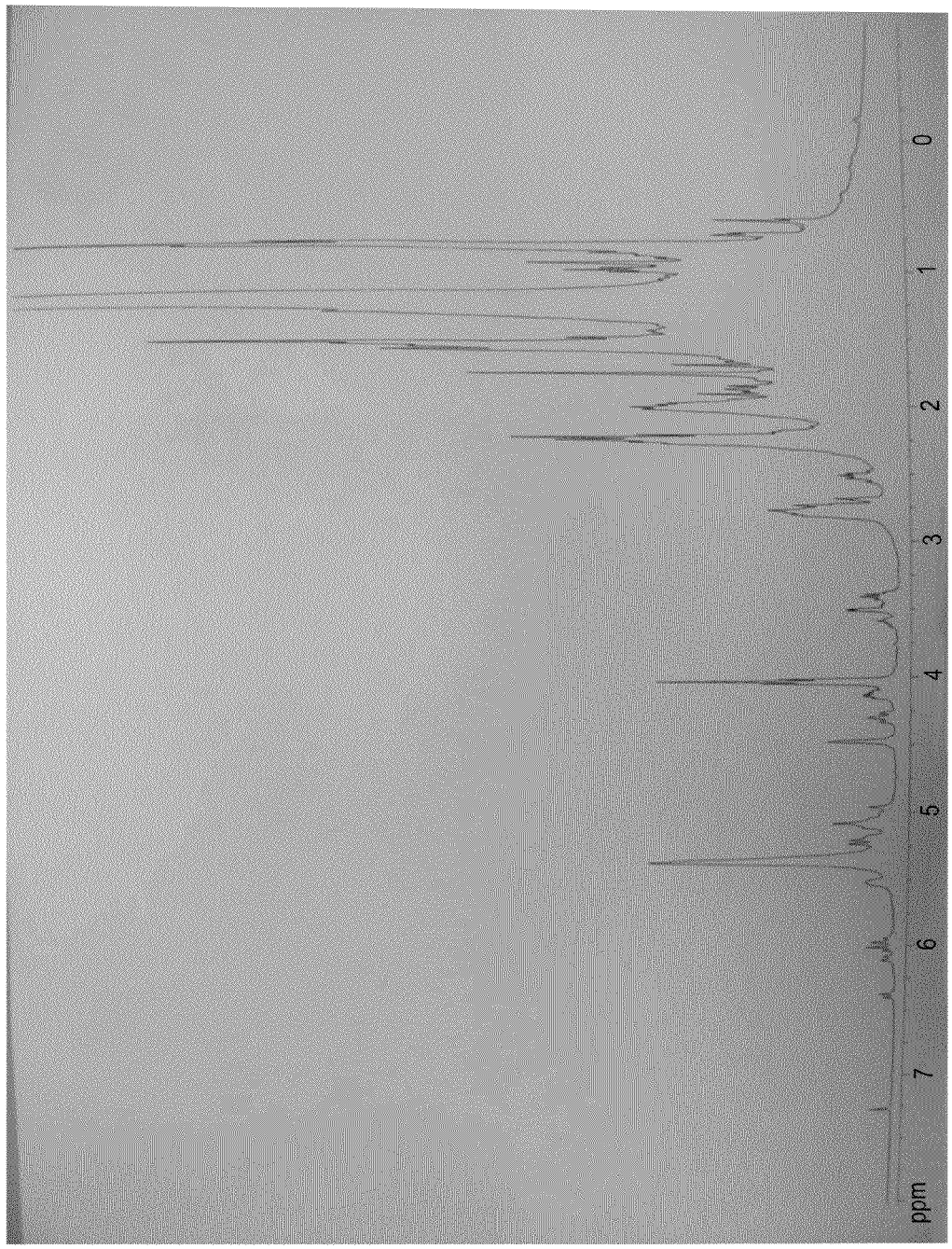

According to one embodiment, the collagen fiber comprises a Nuclear Magnetic Resonance (NMR) spectroscopic profile as shown in FIG. 1.

According to another embodiment, the collagen fiber comprises an amino acid composition as shown in FIG. 2B.

According to yet another embodiment, a fragment of the collagen fiber comprises a major mass at about 4118.47 mass unit (MU).

According to still another embodiment, the collagen fiber comprises a Mass spectroscopy (MS) profile as shown in any one of FIGS. 13A-B-16A-B.

According to yet another embodiment, the isolated collagen fiber of the present invention comprises a stiffness (permanent deformation) about 30-50% lower than that of mammalian collagen.

Thus, for example, a fiber of about 9 μM in diameter comprises a stiffness greater than about 0.34 GPa and less than about 0.54 GPa. According to yet another embodiment, the fiber comprises a stiffness greater than about 0.37 GPa. According to yet another embodiment, the fiber comprises a stiffness greater than about 0.4 GPa. According to yet another embodiment, the fiber comprises a stiffness greater than about 0.44 GPa. According to yet another embodiment, the fiber comprises a stiffness greater than about 0.5 GPa.

According to yet another embodiment, a bundle of collagen fibers of the present invention comprises a stiffness between about 1.5 GPa and 2 GPa.

According to yet another embodiment, the isolated collagen fiber of the present invention comprises a tensile strength about half of mammalian collagen.

Thus, for example a fiber of about 9 μM comprises a tensile strength (breaking point) of more than about 39 MPa. According to yet another embodiment, the tensile strength of the fiber is more than about 41 MPa. According to yet another embodiment, the tensile strength of the fiber is more than about 43 MPa. According to yet another embodiment, the tensile strength of the fiber is more than about 45 MPa. According to yet another embodiment, the tensile strength of the fiber is more than about 47 MPa. According to yet another embodiment, the tensile strength of the fiber is more than about 49 MPa. According to yet another embodiment, the tensile strength of the fiber is more than about 51 MPa. According to yet another embodiment, the tensile strength of the fiber is more than about 53 MPa. According to yet another embodiment, the tensile strength of the fiber is more than about 55 MPa. According to yet another embodiment, the tensile strength of the fiber is more than about 57 MPa. According to yet another embodiment, the tensile strength of the fiber is more than about 59 MPa. According to yet another embodiment, the tensile strength of the fiber is more than about 61 MPa.

It will be appreciated that the collagen fiber of the present invention typically comprises three polypeptide chains (alpha chains), wrapped in rope like fashion to form a tight, triple helix structure. According to one embodiment, each alpha chain of the triple helix is separated by the next by a distance of about 100 nm.

The triple helix of the collagen of the present invention is typically wound in such a way that peptide bonds linking adjacent amino acids are buried within the interior of the molecule, such that the collagen molecules are resistant to attack by proteases, such as pepsin. According to one embodiment, the winding is such that the collagen of the present invention is resistant to degradation by both trypsin and/or collagenase.

As used herein, the phrase "resistant to degradation" refers to the inability of the collagen molecule to fully degrade into individual amino acid components.

It will be appreciated that crosslinking may be performed in order to increase the stability or durability of the collagen. Crosslinking of collagen-based materials of the present invention may also be used to suppress the antigenicity of the material in order to prevent the hyperacute rejection reaction. In addition, crosslinking may used to improve mechanical properties and enhance resistance to both mechanical and proteolytic degradation.

Several chemical crosslinking methods for collagen-based materials are known—see for example U.S. Pat. No. 20050136510. These methods typically involve the reaction of a bifunctional reagent (i.e., a spacer) with the amine groups of lysine or hydroxylysine residues on different polypeptide chains or the activation of carboxyl groups of glutamic and aspartic acid residues followed by the reaction with an amine group of another polypeptide chain to give an amide bond. For example, glutaraldehyde (GA), which is a bifunctional aldehyde, or diisocyanates bridge amine groups on two adjacent polypeptide chains to form crosslinks. Another method of crosslinking involves the formation of an acyl azide. The acyl azide method involves the activation of carboxyl groups in the polypeptide chain. The activated groups form crosslinks by reaction with collagen amine groups of another chain.

Also, water-soluble carbodiimides can be used to activate the free carboxyl groups of glutamic and aspartic acid moieties in collagen. Activation of the carboxyl groups with carbodiimides, such as 1-ethyl-3-(3-dimethylaminopropyl) carbodiimide.HCl (EDC), gives O-acylisourea groups. A condensation reaction by nucleophilic attack of a free amine group of a (hydroxy)lysine residue with urea as a leaving group results in formation of an amide crosslink. The O-acylisourea can also be hydrolyzed or rearranged to an N-acylurea, which is much more stable and will not react to form a crosslink. Addition of N-hydroxysuccinimide (NHS) prevents this rearrangement, however. In the presence of NHS, the O-acylisourea can be converted to an NHS activated carboxyl group, which also can react with a free amine group to form a crosslink.

Other methods of crosslinking may also be used to crosslink the collagen of the present invention such as by glycation using different sugars, by Fenton reaction using metal ions such as copper, by lysine oxidase and/or by UV radiation.

To determine the effect of cross-links and the optimal number of cross-links per monomer unit, the resilience of a crosslinked polymer can be measured using methods known in the art. The level of cross-linking can vary provided that the resulting polymer displays the requisite resilient properties. For example, when the cross-linking is by UV-irradiation, the degree of cross-linking is a function of the time and energy of the irradiation. The time required to achieve a desired level of cross-linking may readily be computed by exposing non-cross-linked polymer to the source of radiation for different time intervals and determining the degree of resilience (elastic modulus) of the resulting cross-linked material for each time interval. By this experimentation, it will be possible to determine the irradiation time required to produce a level of resiliency appropriate for a particular application. The extent of cross-linking may be monitored during the reaction or pre-determined by using a measured amount of reactants.

The present inventors have shown that the collagen of the present invention is bestowed with excellent stretching property and mechanical strength without deteriorating a cell adhesion property of collagen. Therefore, application to the uses, where conventional collagen material cannot be applied due to insufficient stretching property or insufficient mechanical strength is expected.

The collagen may be used per se, or as part of a composite material. The components of the composites of the present invention may be attached to, coated on, embedded or impregnated into the collagen of the present invention. In such composites, the collagen may be uncrosslinked, partially crosslined or fully crosslinked. Exemplary components of the composite material include, but are not limited to minerals, pharmaceutical agents (i.e. drugs) polysaccharides and polypeptides.

Exemplary polysaccharides that may be used in composite materials of the present invention include, but are not limited to glycosaminoglycans such as chondroitin sulfate of type A, C, D, or E, dermatan sulfate, keratan sulfate, heparan sulfate, heparin, hyaluronic acid and their derivatives, individually or mixed.

Exemplary polypeptides that may be used in composite materials of the present invention include, but are not limited to silk, elastin and fibronectin.

Exemplary minerals that may be used in composite materials of the present invention include, but are not limited to calcium, magnesium, boron, zinc, copper, manganese, iron, silicon, selenium, phosphorus and sulfur. Methods for preparing collagen mineral composites are well known in the art, see for example WO/2006/118803.

Since the collagen of the present invention has been shown to support cell propagation, the collagen of the present invention, or composites thereof may be used as part of a scaffold.

As used herein, the term "scaffold" refers to a 3D matrix upon which cells may be cultured (i.e., survive and preferably proliferate for a predetermined time period).

The scaffold may be fully comprised of the collagen of the present invention or composites thereof, or may comprise a solid support on which is layered the collagen of the present invention.

A "solid support," as used refers to a three-dimensional matrix or a planar surface (e.g. a cell culture plate) on which cells may be cultured. The solid support can be derived from naturally occurring substances (i.e., protein based) or synthetic substances. Suitable synthetic matrices are described in, e.g., U.S. Pat. Nos. 5,041,138, 5,512,474, and 6,425,222. For example, biodegradable artificial polymers, such as polyglycolic acid, polyorthoester, or polyanhydride can be used for the solid support. Calcium carbonate, aragonite, and porous ceramics (e.g., dense hydroxyapatite ceramic) are also suitable for use in the solid support. Polymers such as polypropylene, polyethylene glycol, and polystyrene can also be used in the solid support.

Therapeutic compounds or agents that modify cellular activity can also be incorporated (e.g. attached to, coated on, embedded or impregnated) into the scaffold material or a portion thereof. In addition, agents that act to increase cell attachment, cell spreading, cell proliferation, cell differentiation and/or cell migration in the scaffold may also be incorporated into the scaffold. Such agents can be biological agents such as an amino acid, peptides, polypeptides, proteins, DNA, RNA, lipids and/or proteoglycans.

Suitable proteins which can be used along with the present invention include, but are not limited to, extracellular matrix proteins [e.g., fibrinogen, collagen, fibronectin, vimentin, microtubule-associated protein 1D, Neurite outgrowth factor (NOF), bacterial cellulose (BC), laminin and gelatin], cell adhesion proteins [e.g., integrin, proteoglycan, glycosaminoglycan, laminin, intercellular adhesion molecule (ICAM) 1, N-CAM, cadherin, tenascin, gicerin, RGD peptide and nerve injury induced protein 2 (ninjurin2)], growth factors [epidermal growth factor, transforming growth factor-α, fibroblast growth factor-acidic, bone morphogenic protein, fibroblast growth factor-basic, erythropoietin, thrombopoietin, hepatocyte growth factor, insulin-like growth factor-I, insulin-like growth factor-II, Interferon-β, platelet-derived growth factor, Vascular Endothelial Growth Factor and angiopeptin], cytokines [e.g., M-CSF, IL-1beta, IL-8, beta-thromboglobulin, EMAP-II, G-CSF and IL-10], proteases [pepsin, low specificity chymotrypsin, high specificity chymotrypsin, trypsin, carboxypeptidases, aminopeptidases, proline-endopeptidase, *Staphylococcus aureus* V8 protease, Proteinase K (PK), aspartic protease, serine proteases, metalloproteases, ADAMTS17, tryptase-gamma, and matriptase-2] and protease substrates.

Additionally and/or alternatively, the scaffolds of the present invention may comprise an antiproliferative agent (e.g., rapamycin, paclitaxel, tranilast, Atorvastatin and trapidil), an immunosuppressant drug (e.g., sirolimus, tacrolimus and Cyclosporine) and/or a non-thrombogenic or anti-adhesive substance (e.g., tissue plasminogen activator, reteplase, TNK-tPA, glycoprotein IIb/IIIa inhibitors, clopidogrel, aspirin, heparin and low molecular weight heparins such as enoxiparin and dalteparin).

Cells which may be seeded on the collagen of the present invention may comprise a heterogeneous population of cells or alternatively the cells may comprise a homogeneous population of cells. Such cells can be for example, stem cells (such as embryonic stem cells, bone marrow stem cells, cord blood cells, mesenchymal stem cells, adult tissue stem cells), progenitor cells, or differentiated cells such as chondrocytes, osteoblasts, connective tissue cells (e.g., fibrocytes, fibroblasts and adipose cells), endothelial and epithelial cells. The cells may be naïve or genetically modified.

According to one embodiment of this aspect of the present invention, the cells are mammalian in origin.

Furthermore, the cells may be of autologous origin or non-autologous origin, such as postpartum-derived cells (as described in U.S. application Ser. Nos. 10/887,012 and 10/887,446). Typically the cells are selected according to the tissue being generated.

As used herein, the term "seeding" refers to plating, placing and/or dropping cells into the scaffold of the present invention. It will be appreciated that the concentration of cells which are seeded on or within the scaffold depends on the type of cells used and the composition of the scaffold itself.

Techniques for seeding cells onto or into a scaffold are well known in the art, and include, without being limited to, static seeding, filtration seeding and centrifugation seeding.

It will be appreciated that to support cell growth, the cells are seeded on the collagen of the present invention in the presence of a culture medium.

The culture medium used by the present invention can be any liquid medium which allows at least cell survival. Such a culture medium can include, for example, salts, sugars, amino acids and minerals in the appropriate concentrations and with various additives and those of skills in the art are capable of determining a suitable culture medium to specific cell types. Non-limiting examples of such culture medium include, phosphate buffered saline, DMEM, MEM, RPMI 1640, McCoy's 5A medium, medium 199 and IMDM (available e.g., from Biological Industries, Beth Ha'emek, Israel; Gibco-Invitrogen Corporation products, Grand Island, N.Y., USA).

The culture medium may be supplemented with various antibiotics (e.g., Penicillin and Streptomycin), growth factors or hormones, specific amino acids (e.g., L-glutamin) cytokines and the like.

The scaffolds of the present invention may be administered to subjects in need thereof for the regeneration of tissue such as connective tissue, muscle tissue such as cardiac tissue and pancreatic tissue. Examples of connective tissues include, but are not limited to, cartilage (including, elastic, hyaline, and fibrocartilage), collagen, adipose tissue, reticular connective tissue, embryonic connective tissues (including mesenchymal connective tissue and mucous connective tissue), tendons, ligaments, and bone.

Since the scaffolds of the present invention may be used to generate tissue thereon, they may be used for treating subjects with diseases characterized by tissue damage or loss.

As used herein, the term "treating" refers to inhibiting or arresting the development of a disease, disorder or condition and/or causing the reduction, remission, or regression of a disease, disorder or condition in an individual suffering from, or diagnosed with, the disease, disorder or condition. Those of skill in the art will be aware of various methodologies and assays which can be used to assess the development of a disease, disorder or condition, and similarly, various methodologies and assays which can be used to assess the reduction, remission or regression of a disease, disorder or condition.

As used herein, the term "subject" refers to mammals, including, but not limited to, humans, canines and horses.

It will be appreciated that the collagen of the present invention comprises a myriad of uses other than for tissue regeneration including, but not limited to treatment of diseases such as interstitial cystitis, scleroderma, and rheumatoid arthritis cosmetic surgery, as a healing aid for burn patients for reconstruction of bone and a wide variety of dental, orthopedic and surgical purposes.

As mentioned, the present invention also contemplates biologically active fragments of the collagen of the present invention.

The collagen of the present invention may be formulated as pharmaceutical and/or cosmetic compositions.

The term "cosmetic composition" as used herein refers to a composition formulated for external application to human or animal skin, nails, or hair for the purpose of beautifying, coloring, conditioning, or protecting the body surface. The present cosmetic composition can be in any form including for example: a gel, cream, lotion, makeup, colored cosmetic formulations, shampoo, hair conditioner, cleanser, toner, aftershave, fragrance, nail enamel, and nail treatment product.

The phrase "colored cosmetic formulation" refers to cosmetics containing pigment including for example eye shadow, lipsticks and glosses, lip and eye pencils, mascara, and blush.

As mentioned, the collagen of the present invention may also be used as a cosmetic agent for treatment of skin and hair.

Thus, the present invention contemplates the collagen of the present invention as a substance which can be topically applied, optionally in combination with other active substance such as for example a vitamin (vitamin A, C, E or their mixtures) or other topically active substances including but not limited to avarol, avarone or plant extracts, such as Extr. Cepae or Extr. *Echinaceae pallidae*. The collagen of the present invention may be formulated as a topical agent in the form of creams, ointments, lotions or gels such as a hydrogels e.g. on the basis of polyacrylate or an oleogel e.g. made of water and Eucerin.

Oleogels comprising both an aqueous and a fatty phase are based particularly on Eucerinum anhydricum, a basis of wool wax alcohols and paraffin, wherein the percentage of water and the basis can vary. Furthermore additional lipophilic components for influencing the consistency can be added, e.g. glycerin, polyethylene glycols of different chain length, e.g. PEG400, plant oils such as almond oil, liquid paraffin, neutral oil and the like. The hydrogels of the present invention can be produced through the use of gel-forming agents and water, wherein the first are selected especially from natural products such as cellulose derivatives, such as cellulose ester and ether, e.g. hydroxyethyl-hydroxypropyl derivatives, e.g. tylose, or also from synthetic products such as polyacrylic acid derivatives, such as Carbopol or Carbomer, e.g. P934, P940, P941. They can be produced or polymerized based on known regulations, from alcoholic suspensions by adding bases for gel formation.

Exemplary amounts of collagen in the gel include 0.01-30 g per 100 g of gel, 0.01-10 g per 100 g of gel, 0.01-8 g per 100 g of gel, 0.1-5 g per 100 g of gel.

The cosmetic composition may comprise other agents capable of conditioning the body surface including, for example humectants; emollients; oils including for example mineral oil; and shine enhancers including for example dimethicone and cyclomethicone. The present conditioning agents may be included in any of the present pharmacological and/or cosmetic compositions.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the collagen accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, inrtaperitoneal, intranasal, or intraocular injections.

Alternately, one may administer the pharmaceutical composition in a local rather than systemic manner, for example, via injection of the pharmaceutical composition directly into a tissue region of a patient.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuos infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients (collagen) effective to prevent, alleviate or ameliorate symptoms of a disorder (e.g., skin disease).

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p.1).

Dosage amount and interval may be adjusted individually to provide tissue levels of the active ingredient are sufficient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

Whilst analyzing the coral-derived collagen of the present invention, the present inventors have devised a novel approach to farming thereof.

Thus, according to another aspect of the present invention, there is provided a method of farming a soft coral, the method comprising:

(a) attaching the soft coral to a clay surface and (b) growing the soft coral on the clay surface under conditions which support propagation, thereby farming the soft coral.

As used herein, the phrase "soft coral" refers to a coral comprising polyps of eight pinnate tentacles. Typically, the soft coral of the present invention lack a hard external skeleton.

Exemplary soft corals are provided in Table 1 herein below.

TABLE 1

| Class/Subclass | Order | Suborder | Family | Genus | Common Names |
|---|---|---|---|---|---|
| Anthozoa/Octocorallia | Alcyonacea | Alcyoniina | Alcyoniidae | *Cladiella*, *Lobophytum*, *Sinularia*, *Sarcophyton* | Leather |
| " | " | " | Nephtheidae | *Dendronephthya*, *Nephthea*, *Paralemnalia*, *Scleronephthya* | Tree, Cauliflower, Carnation |
| " | " | " | Xeniidae | *Xenia* | Pulse |
| " | Helioporacea | " | Helioporidae | *Heliopora* | Blue, Ridge |

According to one embodiment the soft coral is of the genus *Sarcophyton*, such as for example *Sarcophyton* sp. and *Sarcophyton glaucum*.

The soft coral may be attached to a clay surface using any method known in the art, including for example tethering (e.g. plastic ties, rubber bands, wire or thread, stitches, suspension; adhering (e.g. cyanoacrylate/super glue); capturing (e.g. cementing and epoxying); and impaling (e.g. drilling, pegging and spearing).

The soft coral may be attached to the clay surface immediately following retrieval from a reef or alternatively may be processed (e.g. by cutting) prior to attachment. According to one embodiment, the soft coral is cut up into pieces of less than about 50 mm$^2$ and greater than about 25 mm$^2$.

Exemplary conditions for propagating the soft coral comprise a water temperature at a range of about 20-26° C. under a light intensity range of about 35-130 μE.

According to one embodiment the pH of the water in which the soft coral is propagated is about 8.2.

According to one embodiment when the temperature is about 20° C., the light intensity is about 230 μE.

According to one embodiment when the temperature is about 26° C., the light intensity is about 250 μE.

According to this aspect of the present invention, a soft coral may be propagated for at least six months, at least one year or even longer. An increase of volume of the soft coral cuttings may be as much as X 60 following propagation after 8-12 months, according to the method of the present invention.

As used herein the term "about" refers to ±10%.

The terms "comprises", "comprising", "includes", "including", "having" and their conjugates mean "including but not limited to".

The term "consisting of means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683, 202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Protein Analysis of Fibers from the Soft Coral *Sarcophyton* Sp.

Materials and Methods

Extraction of Fibers from the Soft Coral *Sarcophyton* Sp.:

Samples of the soft coral *Sarcophyton* sp. were collected from the Red Sea and transported frozen to the laboratory. Fibers were mechanically removed from the frozen coral samples.

NMR Analysis:

Collagen fibers ca. 25 mg, were hydrolyzed in 6 N HCl (mL), overnight at 110° C. The acid was then removed under vacuum and the residue dissolved in D2O (0.5 mL). Proton and carbon NMR were measured in 500 MHz and 100 MHz NMR machines, respectively. The spectra are characteristic for hydrolyzate of a peptide, namely, a mixture of amino acids.

Amino Acid Analysis:

Waters PicoTag Work Station for gas phase Hydrolysis Hewlet Packard 1090 HPLC equipped with Diode array Detector and autoinjector with a PC based Chemstation database, utilizing Amino Quant chemistry was used for the analysis. In addition, Waters 2690 Alliance HPLC equipped with fluorescence and Diode Array detectors and autoinjector, utilizing AccQ.Tag and or Pico Tag chemistries for the analysis of Hydrolizates and some physiological Amino acids was used.

Results

Proton and carbon NMR analysis showed that the fibers contain a complex mixture of amino acids, thus indicating that they are composed of proteins (FIG. 1). Amino acid analysis further confirmed the presence of amino acids typical to collagen (e.g., high concentration of Glycine)—FIGS. 2A-B. Enzymes capable of degrading mammalian collagen were not effective on the collagen of the present invention indicating that the latter comprises a different structure to other animal collagens.

Example 2

Mechanical Characterization of Fibers from the Soft Coral *Sarcophyton* Sp.

Materials and Methods

Atomic Force Microscopy:

Atomic force microscopy was performed on a Digital Instruments Dimension 3000 atomic force microscope. Images were taken at 256×256 resolutions in air contact mode. Samples were extracted from mailed specimens with micro dissecting spring scissors and mounted on freshly-cleaved mica with a protocol similar to that of (Wang et al., 2003, Diabetes Metababolism Research and Reviews 19(4): 288-98; Layton et al., 2004, Journal of Biomechanics 37(6): 879-88).

A total of twelve images were taken as summarized in Table 2.

TABLE 2

| Sample number | description | images taken |
| --- | --- | --- |
| 010-03-1 | purified collagen | 5 |
| 010-03-2 | small fixed sample | 4 |
| 010-03-3 | large unfixed sample | 3 |

Raman Spectroscopy:

Raman Spectroscopy was performed with a Raman RM1000.

Mechanical Testing:

Mechanical testing was performed on the isolated collagen sample. The sample was taken from the −20° C. storage, and gently dissected with two fine dissecting tweezers so that a single fibrillar portion approximately 100 μm in diameter and 15 mm long was isolated. The fiber appeared to unwind from the sample in a manner similar to that of a beehive hairdo popular in the United States in the 1960's.

Once the specimen was isolated, it was imaged in bright-field on an Olympus IX81 inverted microscope in air. A total of 25 cross sectional measurements were taken on a total of 17 images. An example of such an image is presented in FIG. 7. The sample was clamped from the bottom of a Fisher Scientific scientific balance manufactured by Denver Instruments. The device has a maximum load of 1 N and a resolution of 1 μN and pulled from the bottom in tension with a micropositioner with a resolution of 10 μm. The specimen was pulled in increments of 10 μm to a total displacement of 120 μm, or just under 1% strain. At each strain increment the displacement was held constant for approximately 80 seconds. In between displacements, the specimen was allowed to relax for approximately 20 seconds. During the latter displacements, some stress relaxation became increasingly evident. At displacements of 100 and 120 μm failure events became apparent, perhaps due to sliding among individual fibers.

Results

The images obtained following atomic force microscopy are presented in FIGS. 3-5.

FIG. 3 is an image of isolated collagen. A 64-nm spacing was not detected in these fibrils. A faint hint of ~100 nm spacing was however found in the fibril marked with a * in FIG. 3. FIGS. 4A-B are images from small fixed sample illustrating that no fibrillar organization is present. FIG. 5 is an image from a large unfixed sample. Probe placement was difficult and no fibrillar organization was present at the 3 μm scale.

A summary of the peaks found in sample 010-03-1 following Raman spectroscopy is given in Table 3. These are summarized from Dong, R., et al [Spectrochim Acta A Mol Biomol Spectrosc 60(3): 557-61] and Frushour, B. G., et al [Biopolymers 14(2): 379-91].

TABLE 3

| |
| --- |
| 1737 |
| 1607 (Phe) |
| 1586 (Pro) |
| 1454 δ(CH3, CH2) |
| 1385 |
| 1306 δ(CH2) |
| 1166 |
| 1122 ν(CCC) |
| 1081 |
| 1046 |
| 914 ν(C—N) pro |
| 961 Amide III |
| 852 ν(C-C) of Pro ring |
| 835 |
| 818 ν(C-C) of backbone or ν(CC) |
| 771 |
| 751 |
| 657 |
| 605 |
| 564 |
| 542 |
| 518 |

The spectroscopy results are shown in FIG. 6. Peculiar to this sample is the absence of the peaks at 1670 corresponding to the amide I bonds and the presence of the peak at 1746 corresponding to the C=O bond.

Mechanical Testing:

Raw force-time data is illustrated in FIG. 8. The raw-force time data was then converted to force-displacement data by plotting maximum force attained at each displacement, as illustrated in FIG. 9.

The force displacement curve was then converted to a stress-strain curve according to: $\sigma = F/A$, where A is the average initial cross-sectional area calculated according to: $A = \phi \pi d^2/4$, where $\phi = 0.5$ is the approximated volume fraction and d is the average bundle diameter measured from the optical images obtained. Strain was defined as: $\epsilon = \Delta/L$, where $\Delta$ is the displacement and L is the initial specimen length. A high and a low elastic modulus were also determined based on:

$$E_{LOW} = \sigma_{80} - \sigma_{10}/\epsilon_{80} - \epsilon_{10}$$

$$E_{HIGH} = \sigma_{120} - \sigma_{80}/\epsilon_{120} - \epsilon_{80}$$

This resulted in an ELOW of 20.6 MPa and an EHIGH of 52.6 MPa.

The stress/strain curve is presented in FIG. 10.

Example 3

MALDI MS Analysis

Materials and Methods

Desalting was performed by C18 spin cartridges. Each sample was diluted to 1 pmol/μl and MALDI MS was performed to analyze the masses present. The samples comprised approximately 100 μg in the first sample and 81.5 μg in the second sample.

Results

MALDI MS analysis indicated that the samples comprised one major mass at 4118.47 in both samples. FIGS. 11-16 illustrate amino acid normalization results for two samples.

Example 4

Comparison of the Mechanical Properties of the Collagen of the Present Invention and Other Animal Collagens Materials and Methods Sample Preparation:
Fibers were mechanically removed from frozen coral samples by tweezers and were rolled by an electrical motor to bundles.

Preparing the System:
The sample were frozen (−20° C.) until the day of the experiment. Prior to the experiment, the sample was defrosted for about one hour in distilled water (DW) at room temperature. The sample was weighed, measured and attached at both ends to Perspex clamps, designed to allow for stretching in the Instron testing machine. During the installation, measures were taken to minimize axial stretching of the sample, and to keep the sample moist. It must be noted that in some of the samples, the presence of black nucleolus-like structures were noticed, but they were not included in the reference length of the sample. The sample was installed in an experimental chamber containing DW, and attached by means of the clamps to the Instron instrument (Load cell—5N). The sample was immersed in a relaxed (un-stretched) state for ca. ½ h.

The Experimental Layout:
Prior to the initiation of the experiment, the undulated sample was extended until becoming straight but not stretched, and its reference length was measured. During the experiment, the sample underwent an elongation profile which included N loading cycles. In each cycle the sample was stretched to an elongation level ΔL at a constant rate SR. Later, the stretch was removed at the same rate as illustrated in FIG. 17. The loading protocol and the measured load were sampled by the Merlin program (of Instron) at a sampling frequency of 50 Hz.

The Experimental Protocols:
Experiment 1
Data:
Sample number: 4.
Number of fibers in sample ($N_f$): 2750.
Average fiber diameter ($d_f$ [μm]): 2.3.
Reference length ($L_0$ [mm]): 48.
Loading Profiles:
A. Number of cycles (N): 10.
Strain rate (SR[%/sec]): 0.5.
Maximal strain ($e_0$ [%]): 17.3.
B. Number of cycles (N): 2.
Strain rate (SR[%/sec]): 0.5.
Maximal strain ($e_0$ [%]): 34.5.

In this experiment, the measurements were conducted using a load cell of 100 N. Due to the low magnitude of the measured forces, a large measurement noise is expected. According to the information provided, this sample might have disaggregated during its wrapping.

Experiment 2
Data:
Sample number: 1.
Number of fibers in sample ($N_f$): 1800.
Average fiber diameter ($d_f$ [μm]): 2.3.
Reference length ($L_0$ [mm]): 47.
Loading Profiles:
A. Number of cycles (N): 5.
Strain rate (SR[%/sec]): 0.5.
Maximal strain ($e_0$ [%]): 17.3.
B. Number of cycles (N): 2.
Strain rate (SR[%/sec]): 0.5.
Maximal strain ($e_0$ [%]): 22.

Results

Results of the experiment include data of time (sec), extension (mm) and load (N). For analyzing the results in a manner which is independent of the sample dimensions, the elongation and load were respectively transformed to strain (e) and stress (s).

The large deformations axial strain of the sample is given by:

$$e = 0.5 \cdot (\lambda^2 - 1) \tag{1}$$

where λ, the extension ratio, is given by:

$$\lambda = \frac{L}{L_0} = \frac{L_0 + \text{extension}}{L_0} = 1 + \frac{\text{extension}}{L_0} \tag{2}$$

The axial second Piola-Kirchoff stress of the sample is given by:

$$s = \frac{F}{\lambda \cdot A_0} \text{[Pa]} \tag{3}$$

where F [in Newton] is the load, and $-A_b$ [m$^2$] is the cross-sectional area of the sample (the fiber bundle) calculated by:

$$A_b = N_f \cdot A_f = N_f \cdot \pi \left(\frac{d_f}{2}\right)^2 \tag{4}$$

where $N_f$ is the number of fibers in a sample and $d_f$ is the average fiber diameter.

Experiment 1:

From observation of the strain-stress curve obtained under loading profile A (FIG. 18), the viscoelastic character of the sample can be clearly noted: the hysteresis loop and the decrease in stress values for the same strain value between consecutive cycles. This reduction in stress values became moderate with the increase in the number of cycles until a stable response was obtained. Thus the stable response was measured in the final loading cycle (FIG. 19).

It is clear that the overall response is not a linear one. However, it seems that starting from a certain strain level, there is a linear relationship between stress and strain. Linear regression to the high range of strain (17.3%-15.3%) data shows very good correlation ($R^2$=0.999). The estimated slope is 1.765 GPa and is an indication of the stiffness of the sample. In addition, although a correlation analysis at different strain ranges may yield a high $R^2$ values, it will be characterized by a different slope (stiffness) values.

In order to test whether the curve indeed has a linear section, the data was numerically differentiated. The resulting derivative is presented in FIG. 20.

Numeric differentiation is known to add noise. However, it is possible to observe that the value of the derivative increases throughout the experimental stretch range. Hence, from these data it is impossible to conclude that there is indeed a linear relationship between stress and strain within the strain range used in this protocol.

In order to test the possibility that the linear region occurs at higher strain levels, the sample must be stretched to higher strains. This goal is achieved by loading profile B.

FIG. 21 presents the stress-strain curve obtained under loading profile B. Three different zones can be identified from the stretching phase of the first cycle: 1. A convex non-linear elevation in stress with increasing strain, 2. A zone of linear stress-strain relationship, 3. A concave non-linear stress-strain zone. The thirds zone is most likely a result of a mechanical failure of some of the fibers. Stretching to higher strains will eventually lead to failure of all fibers until the stress reduces to zero (tear of the sample). Due to the failure of some of the fibers, the number of active fibers within a sample is unknown (torn fibers will no longer carry load) and thus data from subsequent loading cycles can no longer be directly related to the fibers' properties (since they relate to a sample with fewer fibers). Therefore only data from the first loading cycle was used (FIG. 22).

The derivative of the curve is presented in FIG. 23. It appears that there is indeed a zone in which the relationship between stress and strain is linear. Running a linear regression in this zone yields a very good correlation and a slope (stiffness) of 1.994 GPa.

Experiment 2:

The results of loading profile A are presented in FIGS. 24-25. Similarly to the previous experiment, a zone of linear stress-strain zone is not apparent. The slope close to the maximal strain used is 1.627 GPa.

Under loading profile B (FIGS. 26-27), three zones can again be identified in the stress-strain curve. But in contrast to the results of experiment #1, it is difficult to conclude with certainty about the existence of a linear zone from the derivative of the stress-strain data. By running a linear regression near the strain level corresponding to the highest derivative, a slope value of 1.63 GPa is obtained.

Discussion

From the preliminary results presented here, it seems that coral fibers have an impressive stretching ability. The fiber bundle can be stretched to high strains (17-20%) without failing or undergoing irreversible damage. According to the literature, mammalian collagen fibers can be reversibly stretched to strains of only about 8-10% without fibers' failure [Fung Y. C., 1993, Biomechanics: Mechanical Properties of Living Tissue, Springer-Verlag, New York, N.Y. pp. 255-260; Sverdlik A., Lanir Y., 2002, J. Biomech. Eng. Trans. ASME., 124, pp. 78-84].

As opposed to the tendon, a natural source of type 1 collagen, the sample in the present study were artificially prepared by wrapping the fibers into a thick bundle in order to make the stretching load high enough to be reliably measurable. Since the main interest is in characterizing the properties of a single fiber, the stiffness of the fiber must be estimated from the stiffness of the sample (which was estimated by data analysis). Therefore the number and diameters of fibers within the sample must be determined.

In the tendon, it is known that the collagen fibers are non-uniformly undulated and that the non-linearity of the stress-strain curve results from gradual recruitment of the fibers and not necessarily from lack of linearity of the stress-strain relationship of a single fiber [Fung Y. C., 1993, Biomechanics: Mechanical Properties of Living Tissue, Springer-Verlag, New York, N.Y. pp. 255-260; Sverdlik A., Lanir Y., 2002, J. Biomech. Eng. Trans. ASME., 124, pp. 78-84].

Moreover, since the stress-strain curve is characterized by a linear behavior at high strain levels, it is likely that a single fiber is linear and that the lack of linearity results only from gradual recruitment.

From the present results, it appears that there is a zone where a linear relationship between stress and stain exists.

Assuming this is true, and all fibers are recruited and active, then the overall stiffness estimate can be used as a measure of the fiber stiffness:

For the first experiment:

$$K_f = K_b = 1.994 \text{ GPa}$$

For the second experiment:

$$K_f = K_b = 1.63 \text{ GPa}$$

The stiffness data reported in the literature for mammalian collagen fibers are in the range of $K_{Collagen} \approx 0.9 \div 1.8$ GPa [Fung Y. C., 1993, Biomechanics: Mechanical Properties of Living Tissue, Springer-Verlag, New York, N.Y. pp. 255-260; Sverdlik A., Lanir Y., 2002, J. Biomech. Eng. Trans. ASME., 124, pp. 78-84].

Summary

From the above described investigation of the coral fibers, two prominent findings can be pointed out:

A. The coral fibers have a high reversible extensibility compared with mammalian collagen fibers. (The coral fibers can be reversibly stretched to strain 2-3 fold greater than collagen fibers).

B. The stiffness of the coral fibers is at the top range of the reported stiffness range for mammal collagen fibers.

Example 5

Light Microscopy and Electron Microscopy Analysis of the Collagen of the Present Invention Materials and Methods In order to examine cellular aspects of the soft coral's light, scanning and transmission electron microscopy (SEM, TEM)

were applied. Random samples were removed from pieces of colonies that were preserved in 2.5% glutaraldehyde in seawater. The samples were decalcified in a mixture of equal volumes of formic acid (50%) and sodium citrate (15%) for 30 minutes and then placed back in 2.5% glutaraldehyde. Samples for light microscopy were placed in Petri dishes (6 cm diameter) and embedded in 2% agarose (50° C.) in distilled water. Following its solidification, rectangular pieces closely fitting around each sample were cut out and transferred to 70% ethanol. This procedure was conducted in order to maintain the natural orientation of the primary polyps while sectioning them, thus enabling examination in respect to various parts of the colony. Following dehydration through a graded series of ethyl alcohol, the samples were embedded in Paraplast (Monoject Scientific) and sections 8 µm thick were cut and stained in hematoxylin and eosin and Masson for visualization of collagen in the tissue. Samples for SEM and TEM were dehydrated through a graded series of ethyl alcohols. Samples for SEM were fractured in order to expose their internal parts, critically point dried with liquid $CO_2$ and then coated with gold. Material was examined under JEOL JSM 840A SEM operated at 25 kV. Material for TEM embedded in Epon and the sections were stained with both uranyl acetate and lead citrate. The micrographs were studied with Jeol 1200 EX electron microscope.

Results

Light microscopy and electron microscopy (SEM and TEM) were performed on the coral tissue demonstrating fibers in the coenenchyme (mesoglea) of the coral arranged as distinct multilayer bundles in the periphery of the calcium carbonate skeletal elements (=sclerites) of the coral as illustrated in FIGS. 28A-D. Fiber producing cells were identified and fibers were visualized within intracellular vesicles. SEM micrographs illustrated in FIGS. 29A-D demonstrated the unique helical nature of the fibers.

Example 6

Use of the Fibers of the Present Invention as Scaffold for Cell Growth

Materials and Methods

Preosteogenic MBA-15 Cells:
Preosteogenic MBA-15 cells were loaded on the collagen fibers of the present invention. Cells were cultured in growth medium Dulbeccos Modified Essential Medium (DMEM) (Gibco, USA) with addition of 10% heat-inactivated fetal calf serum (FCS) (Sigma, USA), 1% glutamine, and 1% antibiotics and maintained in 5% $CO_2$ at 37° C. $5 \times 10^4$ cells/ml were plated on the polymer and tested after 48 hrs for their interaction with the substrate.
Scanning Electron Microscopy (SEM) Analysis:
The surfaces of the films with or without cells were observed using a Scanning Electron Microscope (SEM, Jeol JEM 6400) at accelerating voltage of 5 kV. Sample preparation included fixation in 3% glutaraldehyde (pH 7.4) for 4 hours, immersion in PBS containing 5.4% sucrose for overnight, dehydration with a graded ethanol series, and drying. The SEM samples were Au/Pd sputtered prior to observation.
Transplantation of Bone Marrow Cells:
Bone marrow cells were loaded on the collagen fibers of the present invention. Femur was cleaned from soft tissue and cells were flushed out with syringe. Cells were allowed to adhere for one hour in vitro and then were implanted subcutanously in rats.

Results

The prosteogenic cells adhered to the collagen surface and were maintained on this natural scaffold in vitro as illustrated in FIGS. 30A-C.
Bone marrow cells adhered, proliferate and formed new tissue following transplantation that allow the evaluation of the fibers as a scaffolding biomaterial for cell growth and tissue regeneration. The in vivo subcutaneous transplantation of the fibers revealed their immunocompetent nature i.e. no inflammatory reaction was observed in the tissue formed on the scaffold of collagen fibers. As illustrated in FIGS. 31A-B, the tissue formed is fibrous with areas of higher matrix content (circle) which indicates deposition, possibly as new osteoid.
In addition, the collagen scaffold alone (without cells) implanted subcutaneously was adsorbed/degraded within two weeks. When bone marrow cells were added to the collagen scaffold of the present invention and implanted subcutaneously, fewer osteoclastic cells were observed as compared to that observed when a commercial collagen scaffold seeded with bone marrow cells was implanted subcutaneously. Further, less effective fibro-osteogenic tissue formation was observed with the commercial collagen scaffold.

Example 7

Propagation of the Soft Coral Genus *Sarcophyton* (Octocorallia, Alcyonacea)

Species of the soft coral genus *Sarcophyton* (Octocorallia, Alcyonacea) have a wide Indo-Pacific distribution. They are known for their content of diverse natural compounds. *Sarcophyton glaucum* is the most widely distributed species within the genus, and it is abundant on the Red Sea reefs. The present example illustrates the development of a protocol for propagation of *S. glaucum* colonies obtained from Eilat (northern Red Sea, Israel), in a closed system.

Materials and Methods

The first series of experiments conducted in the study examined: (1) the optimal size of the cuttings to be used for mass colony formation, (2) the appropriate base type and (3) the best glue to maximize their survival. Cuttings soft coral genus *Sarcophyton* (Octocorallia, Alcyonacea) were placed in an experimental closed system containing 4 $m^3$ of artificial-seawater that fed 24 test tanks (30 l each) enabling a series of controlled conditions for each experiment. The survival, biomass, organic weight and morphology of the cuttings were monitored for 70-80 days of the experiments under different temperature, light, salinity and feeding regimes.

Results

It was found that cuttings with a surface area of 36 $mm^2$ polyp-bearing part (polyparium), glued with Cyanoacrylate glue to clay-made bases yielded the highest survival rate.
At low temperature (20° C.) the highest organic biomass was obtained. It is suggested that, under these conditions, the calcification rate might decrease, thus increasing the organic biomass. Under a high light intensity of 250 µE, growth rates and dry weight of the cuttings increased. Under a mid-range light intensity (35-130 μE) survival and organic biomass was higher than under the lowest and the highest ones (20 and 250 μE). It is possible that these results were due to low density of the symbiotic zooxanthellae, that under low light intensities do not allow efficient photosynthesis, and to photoinhibition taking place under high light intensities.

Salinity did not affect survival, biomass and organic weight of the cuttings over time.

Cuttings that were frequently fed by brine shrimps-*Artemia nauplei* (every 2 days) had the lowest organic weight. It is suggested that the time required for digestion by the polyps may control the rate of food capture and, therefore, frequent feeding will not benefit the cuttings and may even harm them, due to the decomposition of unconsumed food in the water that impairs the water quality.

Observations derived from the experiments indicated that the volume of water in which the cuttings are reared may influence their ability to adhere to the substrate. Experiments showed that cuttings maintained in a small water volume (20 or 70 l.) attached to the clay bases faster than cuttings kept in 2,880 liter aquaria.

In order to examine the relationship between colony size and percentage of organic matter, reefal colonies of *S. glaucum*, of three size classes (5-7 cm, 10-15 cm, 20 cm disc diameter) were examined. The lowest percentage of organic matter (10%) was found in the small colonies, which were also used in the current study for preparation of the cuttings. The percentage of organic matter in cuttings reared in the closed system was noticeably higher than that found in all the three size groups collected from the sea. It is possible that reefal colonies have more calcareous material in the coral sclerites, facilitating their adaptation to water currents, waves and predation.

In a concluding experiment cuttings were reared under a culturing protocol based on the results of the above-mentioned experiments. The results were compared with those obtained in an open seawater system and in the reef. It was concluded that a closed system increased the percentage of organic matter of the cuttings. Although cuttings that were farmed in the sea had a slightly higher dry weight compared to those farmed in closed system, the former had a much higher percentage of organic matter, which is extremely important for the pharmaceutical industry. Cuttings from the closed system had a higher dry weight and organic matter percentage compared to those farmed in the open system.

Example 8

Composition of the Soft Coral Genus *Sarcophyton glaucum* (Octocorallia, Alcyonacea) Following Farming in a Closed System Results NMR (Nuclear Magnetic Resonance) analysis revealed different patterns of natural compounds in cuttings reared in the three different environments mentioned above (i.e., closed seawater system, open seawater system and on the reef). Since all cuttings were obtained from the same parent colonies, it is suggested that the environmental conditions of the experimental set up determined the content of the natural compounds.

Cuttings reared in the sea were characterized by a semi-solid rigidity and had a hemispheric polyparium and short polyps. Cuttings from the closed system had long polyps, a long colony stalk and a flat polyparium.

Conclusion

The results of the experiments described in Examples 7 and 8, illustrate the advantages of a closed system for culturing of *S. glaucum*.

Example 9

Structural Features of the Soft Coral Collagen Fibers

In order to analyze the structural features of the soft coral collagen fibers of one embodiment of the present invention, histological sections of *Sarcophyton* sp. were treated with collagen specific staining Masson Blue. In addition, the collagen fibers of one embodiment of the present invention were analyzed using transmission electron microscopy (TEM).

Results

The results of the histological staining of the fibers are provided in FIGS. 32A-B.

The TEM images are provided in FIGS. 33A-B, 34 and 35. In the images the green is collagen fibers and the red is cytoplasm of the soft coral cells.

Example 10

Mechanical Properties of Isolated Collagen Fibers from *Sarcophyton* Sp

Materials and Methods

Sample Preparation:
Bundles of fibers were isolated from the mesoglea of the soft coral *Sarcophyton* sp. by forcipes, and starched on polyethylene plastic cards (1×8 cm) prior to incubation in ethanol (70% in fresh water). The samples were then analyzed.

Experimental System:
Prior to the experiment, samples were rehydrated for one hour in fresh water (FW) at room temperature. Single fibers were isolated from the bundles by forcipes under a dissecting microscope and measured (length and diameter) by light microscope (Nikon, 100×, oil immersion) photography and imaging software (FIG. 36). A single fiber was attached at one end to a stainless steel tensometer beam with a half bridge formed by two semi-conductor strain gages (1 gr=7.45V, max 10 gr) using cynoacrylate glue. The other end of the fiber was fixed to a stainless steel beam maneuvered by micrometer (FIG. 37). During installation, measures were taken to minimize axial stretching of the sample and to keep the sample moist. The sample was installed in an experimental chamber containing FW, and was immersed in a relaxed (un-stretched) state for approximately 30 minutes prior to testing.

Before initiating the experiments, the force transducer beam deflection was measured by pulling a thin, non-flexible copper wire in known increments. The calculated beam deflection was subtracted from all fiber displacement results in order to obtain the true displacement. In the experiments, the undulated sample was extended until it became straight but not stretched, and its reference length was measured by caliber in mm (L initial). Preconditioning to 5% (3 cycles) was performed before the samples underwent elongation profiles of load-unload (4 cycles) or Load to failure, and L0 was measured. Volts output was gained ×1000 and reading was performed by a voltmeter. Micrometer maneuvering and data recording was performed by hand in 100 μM increments and Force (N) was calculated.

Results of the experiment include extension (μm) and load (N). For analyzing the results in a manner that is independent of the sample dimensions, the elongation and load were respectively transformed to strain (e) and stress (s).

s=F/A; e=ΔL/L0, where F [in Newton] is the load, and A=πR² is the cross-sectional area of the sample (the fiber). Data analysis was performed using Microsoft Excel.

Results

Preconditioning:
L0 was obtained from strain-stress curves of preconditioning cycles (FIG. 38).
Average different between L initial and L0 was 0.03±0.0094.
Load-Unload Cycles:
From observation of the strain-stress curves obtained under loading-unloading cycles of 3 samples, the viscoelastic character of the samples can be observed: the hysteresis loop and the decrease in stress values for the same strain value between consecutive cycles (FIG. 39). Average hysteresis for the first cycle was 41.2595±15.5%.
It is clear from FIG. 39 that the overall response is not a linear one. However, it seems that at a certain strain level, there is a linear relationship between stress and strain. Linear regression to the high range of strain (7%-15%), shows very good correlation ($R^2$=0.999). No correlation was found between slope to sample length (p>0.05). The estimated slope is 0.5±0.1 GPa and is an indication of the stiffness of the sample.
Load to Failure:
From the load to failure strain-stress curves of 12 samples, it is clear that the overall response is not a linear one (FIG. 40). Linear regression to the high range of strain (8%-19.4%) shows very good correlation ($R^2$=0.999). No correlation was found between slope to sample length (p>0.05). The estimated slope is 0.44±0.1 GPa and is an indication of the stiffness of the sample. Average load to failure was 49.4±11.7 MPa and average extensibility was 19.4±4.27%.

Conclusion

From the results presented here, it seems that soft coral fibers have an impressive stretching ability. The fibers can be stretched to high strains (19.4±4.27%) without failing or undergoing irreversible damage. According to the literature, mammalian collagen fibers can be reversibly stretched to strains of only about 8-10% without fibers' failure (FIG. 40) (Fung, 1993, Biomechanics: Mechanical Properties of Living Tissue, Springer-Verlag, New York, N.Y. pp. 255-260 which is hereby incorporated by reference) and mesoglea can be stretched to strains of 3.5-6% (Koehl, 1982, Mechanical design of spicule-reinforced connective tissue: stiffness. J. Exp. Biol. 98, 239-267). The stiffness of the coral fibers (0.44±0.1 GPa) is about half to a third lower than reported stiffness range for mammalian collagen fibers (0.9-1.8 GPa) (Sverdlik & Lanir., 2002, J. Biomech. Eng. Trans. ASME., 124, pp. 78-84), and five orders of magnitude bigger then mesoglea (0.01 MPa) (Vogel, 2003, Comparative Biomechanics: Life's Physical World. Princeton: Princeton University Press). Their average load to failure (49.4±11.7 MPa) is about a half of the reported tensile strength for mammalian collagen fibers (100 MPa) (Vogel, 2003, supra) and an order of magnitude bigger than mesoglea (1-2.5 MPa) (Koehl, 1981, supra).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of regenerating connective tissue, the method comprising providing to a subject in need-thereof a scaffold comprising collagen fibers being extracted from a soft coral, wherein a length of said fibers following stretching by about 15%, is identical to a length of said fibers prior to said stretching, thereby regenerating the connective tissue.

2. The method of claim 1, wherein the collagen is comprised in a composite.

3. The method of claim 2, wherein a second component of said composite is selected from the group consisting of a mineral, a polysaccharide and a polypeptide.

4. The method of claim 1, wherein said connective tissue is selected from the group consisting of cartilage, collagen, adipose tissue, reticular connective tissue, embryonic connective tissues, tendons, ligaments, and bone.

5. The method of claim 4, wherein said cartilage is selected from the group consisting of elastic cartilage, hyaline cartilage and fibrocartilage.

6. The method of claim 1, wherein said soft coral is of the *Sarcophyton* genus.

7. The method of claim 1, wherein said collagen fibers have a stiffness about 30-50% lower than that of mammalian collagen.

8. The method of claim 1, wherein said collagen fibers have a tensile strength between about 39-59 MPa.

9. A method of regenerating connective tissue, the method comprising providing to a subject in need-thereof a scaffold comprising collagen fibers being extracted from a soft coral of the *Sarcophyton* genus.

10. The method of claim 9, further comprising seeding cells on the scaffold prior to said providing.

* * * * *